(12) United States Patent
Kountchev et al.

(10) Patent No.: US 11,995,808 B2
(45) Date of Patent: May 28, 2024

(54) METHOD FOR X-RAY DENTAL IMAGE ENHANCEMENT

(71) Applicant: Abova, Inc., Minneapolis, MN (US)

(72) Inventors: Roumen Kountchev, Sofia (BG); Michael McGuire, Prior Lake, MN (US); Peter Vladimirov, Medina, MN (US)

(73) Assignee: Abova, Inc, Minneapolis, MN (US)

( * ) Notice: Subject to any disclaimer, the term of this patent is extended or adjusted under 35 U.S.C. 154(b) by 447 days.

(21) Appl. No.: 17/446,942

(22) Filed: Sep. 3, 2021

(65) Prior Publication Data

US 2022/0076392 A1 Mar. 10, 2022

Related U.S. Application Data

(60) Provisional application No. 63/202,997, filed on Jul. 2, 2021, provisional application No. 63/200,131, filed
(Continued)

(51) Int. Cl.
*A61B 6/14* (2006.01)
*A61B 6/51* (2024.01)
(Continued)

(52) U.S. Cl.
CPC .............. *G06T 5/92* (2024.01); *A61B 6/51* (2024.01); *G06T 5/20* (2013.01); *G06T 5/40* (2013.01);
(Continued)

(58) Field of Classification Search
CPC ........... G06T 5/009; G06T 5/004; G06T 5/20; G06T 5/40; G06T 7/0012; G06T 7/136;
(Continued)

(56) References Cited

U.S. PATENT DOCUMENTS

| 7,327,860 B2 | 2/2008 | Derakhshani et al. |
| 7,840,055 B2 | 11/2010 | Huo |

(Continued)

FOREIGN PATENT DOCUMENTS

| CN | 106485674 A | 3/2017 |
| CN | 107403418 A | 11/2017 |

(Continued)

OTHER PUBLICATIONS

Amiri, S Asadi, "Image quality enhancement in digital panoramic radiograph", Journal of AI and Data Mining, vol. 2, No. 1, (2014), 6 pgs.

(Continued)

*Primary Examiner* — Shefali D Goradia
*Assistant Examiner* — D J Dhooge
(74) *Attorney, Agent, or Firm* — Schwegman Lundberg & Woessner, P.A.

(57) ABSTRACT

Various examples are directed to apparatus and methods for enhancing an X-ray medical image. In one example, a method for X-ray dental images enhancement is provided. The method includes receiving an input image and applying the noise reduction trough Recursive Locally-Adaptive Wiener Filtration (RLA-WF) based on the sliding window, which is calculated following a recursive two-dimensional scheme; contrast enhancement to the filtered image, including using recursive Sliding Window Contrast Limited Adaptive Histogram Equalization (SW-CLAHE) utilizing a Truncation Threshold Surface (TTS) for calculation of the truncation threshold for the local histogram in each sliding window. The method also includes applying sharpness enhancement to the input image, including using Fast Recursive Adaptive Unsharp Masking (FRA-UM) utilizing a sliding window with two or one-dimensional recursion, to obtain a sharpened image. The contrast enhanced image is (Continued)

linearly mixed with the sharpened image using a control coefficient to obtain an output image, and the output image is provided to a display of a user.

22 Claims, 23 Drawing Sheets

Related U.S. Application Data on Feb. 16, 2021, provisional application No. 62/706,727, filed on Sep. 4, 2020.

(51) Int. Cl.
| | |
|---|---|
| *G06T 5/20* | (2006.01) |
| *G06T 5/40* | (2006.01) |
| *G06T 5/75* | (2024.01) |
| *G06T 5/92* | (2024.01) |
| *G06T 7/00* | (2017.01) |
| *G06T 7/136* | (2017.01) |

(52) U.S. Cl.
CPC .............. *G06T 5/75* (2024.01); *G06T 7/0012* (2013.01); *G06T 7/136* (2017.01); *G06T 2207/10116* (2013.01); *G06T 2207/30036* (2013.01)

(58) Field of Classification Search
CPC . G06T 2207/10116; G06T 2207/30036; G06T 5/007; G06T 5/002; A61B 6/14
See application file for complete search history.

(56) References Cited

U.S. PATENT DOCUMENTS

| | | | |
|---|---|---|---|
| 7,840,066 | B1 | 11/2010 | Chen et al. |
| 8,144,959 | B2 | 3/2012 | Zingaretti et al. |
| 8,213,711 | B2 | 7/2012 | Tam et al. |
| 8,340,414 | B2 | 12/2012 | Hogasten et al. |
| 8,433,033 | B2 | 4/2013 | Harata et al. |
| 8,515,196 | B1 | 8/2013 | Hoegasten |
| 8,724,857 | B2 | 5/2014 | Derakhshani et al. |
| 8,861,886 | B2 | 10/2014 | Huo et al. |
| 8,909,508 | B2 | 12/2014 | Hurley et al. |
| 9,262,864 | B2 | 2/2016 | Rohaly et al. |
| 9,280,821 | B1 | 3/2016 | Choe et al. |
| 9,418,408 | B1 | 8/2016 | Thompson |
| 9,427,174 | B2 | 8/2016 | Tuliakov et al. |
| 9,467,704 | B2 | 10/2016 | Ten |
| 9,646,366 | B2 | 5/2017 | Rizi et al. |
| 9,928,592 | B2 | 3/2018 | Xiong et al. |
| 9,971,920 | B2 | 5/2018 | Derakhshani et al. |
| 10,007,971 | B2 | 6/2018 | Xiong et al. |
| 10,108,858 | B2 | 10/2018 | Derakhshani et al. |
| 10,290,108 | B2 | 5/2019 | Zhang et al. |
| 10,311,286 | B2 | 6/2019 | Saripalle et al. |
| 10,420,523 | B2 | 9/2019 | Hoogi et al. |
| 10,485,638 | B2 | 11/2019 | Salah et al. |
| 10,516,865 | B2 | 12/2019 | Sidar et al. |
| 2012/0263366 | A1* | 10/2012 | Huo ......................... G06T 5/009 382/132 |
| 2013/0022287 | A1 | 1/2013 | Hooper |
| 2014/0153793 | A1 | 6/2014 | Goharrizi et al. |
| 2014/0282624 | A1 | 9/2014 | Holt et al. |
| 2016/0302895 | A1 | 10/2016 | Rohaly et al. |
| 2017/0258391 | A1 | 9/2017 | Finn et al. |
| 2017/0262977 | A1 | 9/2017 | Finn et al. |
| 2017/0262979 | A1 | 9/2017 | Xiong et al. |
| 2017/0262985 | A1 | 9/2017 | Finn et al. |
| 2017/0281110 | A1* | 10/2017 | Mandelkern ......... A61B 6/5223 |
| 2018/0189543 | A1 | 7/2018 | Gottemukkula et al. |
| 2018/0353263 | A1 | 12/2018 | Salah et al. |
| 2019/0125493 | A1 | 5/2019 | Salah et al. |
| 2019/0167110 | A1 | 6/2019 | Dan et al. |
| 2019/0191988 | A1 | 6/2019 | Gargeya |
| 2019/0333223 | A1 | 10/2019 | Jiang et al. |
| 2019/0385311 | A1 | 12/2019 | Rivard et al. |
| 2020/0013162 | A1 | 1/2020 | Yum et al. |
| 2020/0048516 | A1 | 2/2020 | Bottiglieri et al. |
| 2020/0065998 | A1 | 2/2020 | Dissanayake et al. |
| 2020/0092526 | A1 | 3/2020 | Sidar et al. |

FOREIGN PATENT DOCUMENTS

| | | | | |
|---|---|---|---|---|
| EP | 1840821 | A1 | 10/2007 | |
| EP | 2226762 | A1 | 9/2010 | |
| IN | 1755CHE2015 | A | 7/2016 | |
| IN | 274690 | B | 8/2016 | |
| IN | 201841029826 | A | 8/2018 | |
| TW | I563473 | B | 12/2016 | |
| WO | WO-2010030159 | A2 | 3/2010 | |
| WO | WO-2010131944 | A2 | 11/2010 | |
| WO | WO-2013130541 | A3 | 6/2015 | |
| WO | WO-2017083709 | A1 * | 5/2017 | ............... A61B 6/14 |
| WO | WO-2017083709 | A1 | 5/2017 | |
| WO | WO-2020044052 | A1 | 3/2020 | |
| WO | WO-2022051775 | A1 | 3/2022 | |

OTHER PUBLICATIONS

Hummel, Robert, "Image Enhancement by Histogram Transformation", Computer Graphic and Image Processing, 6, (1977), 184-195.

Min, Byong Seok, "A Novel Method of Determining Parameters of CLAHE Based on Image Entropy", International Journal of Software Engineering and Its Applications, vol. 7, No. 5, (2013), 113-120.

Mohamed, Youif, "Chapter 5: Research in Medical Imaging Using Image Processing Techniques", Medical Imaging. Principles and Applications. IntechOpen, (2019), 16 pgs.

Zhu, Hui, "Image Contrast Enhancement by Constrained Local Histogram Equalization", Computer Vision and Image Understanding, vol. 73, No. 2, (1999), 281-290.

"International Application Serial No. PCT/US2021/071373, International Search Report dated Jan. 5, 2022", 5 pgs.

"International Application Serial No. PCT/US2021/071373, Written Opinion dated Jan. 5, 2022", 6 pgs.

"Sharpness Evaluation Method without Reference Image (Evaluation Index for Image Sharpness)", [Online]. Retrieved from the Internet: <URL: (Evaluation Index for Image Sharpness) https://www.programmersought.com/article/6056166465>, (Accessed Jun. 2, 2022), 26 pgs.

Aghdasi, F, et al., "Noise filtering for mammographic images", Proceedings of the Annual International Conference of the IEEE Engineering in Medicine and Biology Society: Paris, France, IEEE, New York, NY, USA, (Oct. 29, 1992), 2 pgs.

Ahmad, Siti, et al., "A comparison of image enhancement techniques for dental x-ray image interpretation", GCSE, (2011), 10 pgs.

Ahmad, Siti Arpah, et al., "An Analysis of Image Enhancement Techniques for Dental X-ray Image Interpretation", International Journal of Machine Learning and Computing, (Jan. 2012), 7 pgs.

Ahmad, Siti, et al., "Correlation between Quantitative and Qualitative Analysis on Image Quality of Digital Dental X-ray Images", Journal of Computer Science & Computational Mathematics, vol. 2, Issue 8, (2012), 43-51.

Bae, Unmin, et al., "Fast Adaptive Unsharp Masking with Programmable Mediaprocessors", Journal of Digital Imaging, vol. 16, No. 2, (Jun. 2003), 10 pgs.

Campos, Gabriel, et al., "Machine learning hyper-parameter selection for Contrast Limited Adaptive Histogram Equalization", EURASIP Journal on Image and Video Processing, 59, (2019), 18 pgs.

Georgieva, Veska, et al., "Chapter 7, An Adaptive Enhancement of X-ray Images", Advances in Intelligent Analysis of Medical Data and Decision Support Systems, (2014), 79-88.

Gonzalez, R C, et al., "", Digital Image Processing, Third Edition, Pearson International edition, (2008), 976 pgs.

Ibrahim, Haidi, et al., "Local Contrast Enhancement Utilizing Bidirectional Switching Equalization of Separated and Clipped

(56) References Cited

OTHER PUBLICATIONS

Subhistograms", Mathematical Problems in Engineering, vol. 2014, Article ID 848615, (2014), 11 pgs.

Isaksson, Johan, "FPGA-Accelerated Image Processing Using High Level Synthesis with OpenCL", Master of Science Thesis in Electrical Engineering, (2017), 67 pgs.

Jaya, V L, et al., "IEM: A New Image Enhancement Metric for Contrast and Sharpness Measurements", International Journal of Computer Applications, vol. 79, No. 9, (2013), 9 pgs.

Jin, F, et al., "Adaptive Wiener Filtering of Noisy Images and Image Sequences,", International Conference on Image Processing, (2003), 4 pgs.

Kokufuta, Kentaro, et al., "Real-time processing of contrast limited adaptive histogram equalization on FPGA", 2010 International Conference on Field Programmable Logic and Applications, (2010), 155-158.

Kumari, A, et al., "A Novel Method for Dental Radiographs Contrast Enhancement for Efficient Diagnosis of Dental Diseases", International Journal of Innovative Technology and Exploring Engineering, vol. 8 Issue—4S2, (Mar. 2019), 6 pgs.

Polesel, Andrea, et al., "Image Enhancement via Adaptive Unsharp Masking", IEEE Trans. on Image Processing, vol. 9, No. 3, (2000), 505-510.

Qassim, H, et al., "Brightness Preserving Enhancement for Dental Digital X-ray Images Based on Entropy and Histogram Analysis", Journal of Applied Science and Engineering, vol. 22, No. 1, (2019), 187-194.

Roomi, M, et al., "A Review of Image Contrast Enhancement Methods and Techniques", Research Journal of Applied Sciences, Engineering and Technology 9(5), (2015), 18 pgs.

Rubini, C, et al., "Contrast Enhancement of MRI Images using AHE and CLAHE Techniques", International Journal of Innovative Technology and Exploring Engineering, vol. 9 Issue 2, (Dec. 2019), 2442-2445.

Siti, Arpah Bt Ahmad, et al., "Analysis of image quality based on dentists' perception cognitive analysis and statistical measurements of intra-oral dental radiographs", Biomedical Engineering (ICOBE), 2012 International Conference On, IEEE,, (Feb. 27, 2012), 6 pgs.

Sund, T, et al., "Sliding window adaptive histogram equalization of intraoral radiographs-effect on image quality", Dento-Maxillo-Facial Radiology, Int. Ass. Dento-Maxillo-Facial Radiology, Goteborg, vol. 35, No. 3, (May 2006), 6 pgs.

Thanh, Dang, et al., "A Review on CT and X-Ray Images Denoising Methods", Informatica, 43, (2019), 151-159.

Wan, Minjie, et al., "Infrared Image Enhancement Using Adaptive Histogram Partition and Brightness Correction", Remote Sensing MDPI 10(5), 682, [Online]. Retrieved from the Internet: <URL: https://doi.org/10.3390/rs10050682>, (2018), 34 pgs.

Westin, C, et al., "Adaptive Image Filtering", Handbook of Medical Imaging, Academic Press, (2000), 22 pgs.

Zhou, Y, et al., "Contrast enhancement of medical images using a new version of the World Cup Optimization algorithm", Quantitative Imaging in Medicine and Surgery, vol. 9, No. 9, (2019), 1528-1547.

\* cited by examiner

| -1 | -1 | -1 | -1 | -1 | -1 | -1 |
|---|---|---|---|---|---|---|
| -1 | -1 | -1 | -1 | -1 | -1 | -1 |
| -1 | -1 | -1 | -1 | -1 | -1 | -1 |
| -1 | -1 | -1 | 148 | -1 | -1 | -1 |
| -1 | -1 | -1 | -1 | -1 | -1 | -1 |
| -1 | -1 | -1 | -1 | -1 | -1 | -1 |
| -1 | -1 | -1 | -1 | -1 | -1 | -1 |

1/100

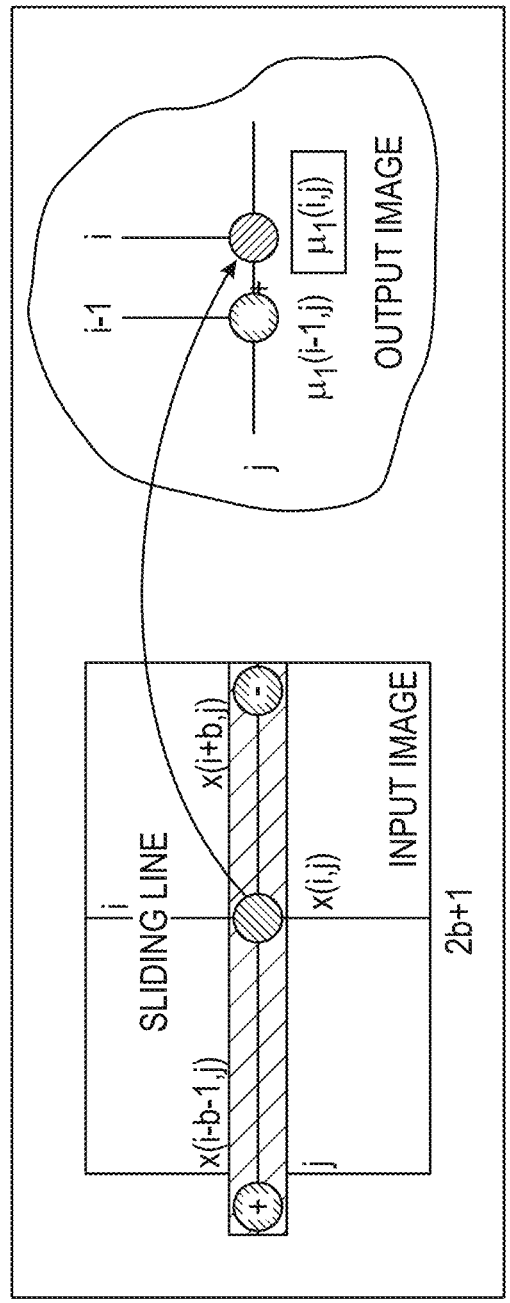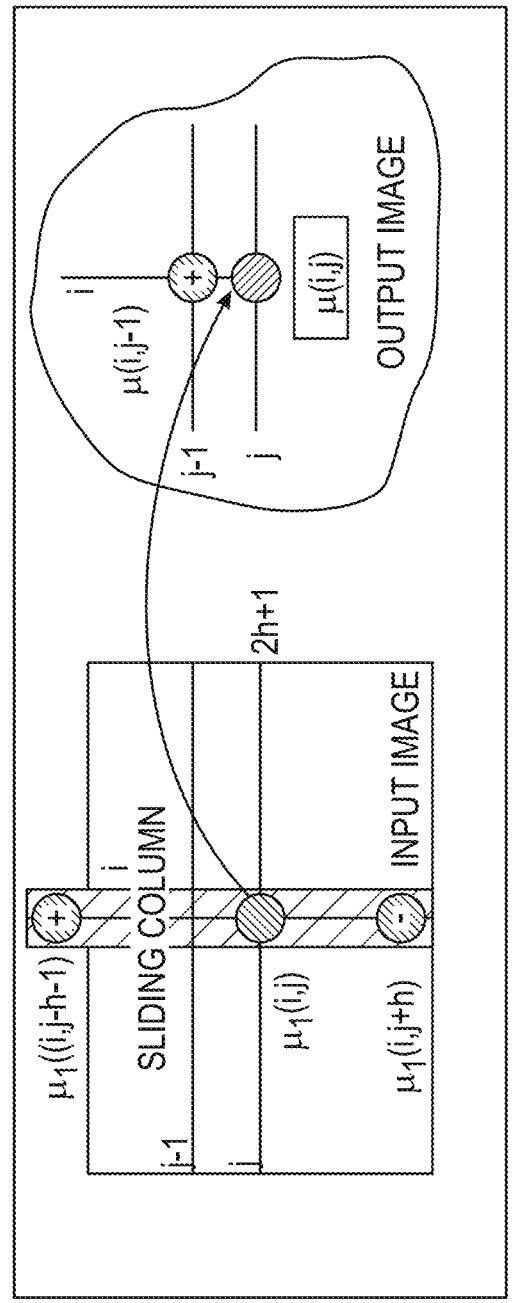
FIG. 18
FIG. 19

INPUT IMAGE - SAMPLE 1

AFTER APPLICATION OF CLAHE FOR THE SAMPLE 1

AFTER APPLICATION OF THE NON-ITERATIVE
RSW-CLAHE AND FRA-UM FOR THE SAMPLE 1

INPUT IMAGE – SAMPLE 2

AFTER APPLICATION OF CLAHE FOR THE SAMPLE 2

AFTER APPLICATION OF THE NON-ITERATIVE
RSW-CLAHE AND FRA-UM FOR THE SAMPLE 2

INPUT DENTAL X-RAY PANORAMIC IMAGE

ENHANCED DENTAL X-RAY PANORAMIC IMAGE BY CLAHE, MSDE=4.20 BITS

ENHANCED IMAGE BY RSW-CLAHE FOR q=0.02 AND c=16, MSDE=138.77BITS

INPUT X-RAY DENTAL PERIAPICAL IMAGE

ENHANCED IMAGE BY CLAHE, MSDE=1.57 BITS

ENHANCED IMAGE BY RSW-CLAHE FOR
q=0.02, c=27, MSDE=82.69 BITS

METHOD FOR X-RAY DENTAL IMAGE ENHANCEMENT

CLAIM OF PRIORITY

This application claims the benefit of priority under 35 U.S.C. § 119(e) of U.S. Provisional Patent Application Ser. No. 62/706,727, filed on Sep. 4, 2020, U.S. Provisional Patent Application Ser. No. 63/200,131, filed on Feb. 16, 2021, and U.S. Provisional Patent Application Ser. No. 63/202,997, filed on Jul. 2, 2021, which are herein incorporated by reference in their entireties.

TECHNICAL FIELD

Embodiments described herein generally relate to X-ray medical image enhancement and, for example and without limitation, to algorithms, apparatus and systems for X-ray dental imaging enhancement.

BACKGROUND

X-ray medical images enable a practitioner to diagnose health problems and develop an appropriate treatment plan to address the diagnosed problems. Medical imaging covers a wide variety of applications. For example, in dental applications enhanced clarity in X-ray dental imaging can provide the practitioner with the best images available to perform an accurate diagnosis. Current methods for enhancing X-ray dental images may excessively amplify noise and result in image distortion. An improved process for X-ray dental imaging enhancement is needed.

SUMMARY

Disclosed herein, among other things, is method for enhancing X-ray dental images. The method includes receiving an input image and applying contrast enhancement to the input image, including using Recursive Locally-Adaptive Wiener Filtration (RLA-WF), Recursive Sliding Window Contrast Limited Histogram Equalization (RSW-CLAHE) utilizing a Truncation Threshold Surface (TTS), and a sliding window to obtain an enhanced input image. The method also includes applying sharpness enhancement to the input image, including using Fast Recursive Adaptive Unsharp Masking (FRA-UM) utilizing the sliding window, to obtain a sharpened image. The enhanced input image is linearly mixed with the sharpened input image using a control coefficient to obtain an output image, and the output image is provided to a display of a user, in various embodiments.

This Summary is an overview of some of the approaches of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

The drawings illustrate generally, by way of example, various embodiments discussed in the present document.

FIG. 18 is an illustration of a spatial arrangement of pixels in a sliding line used for a recursive calculation in horizontal direction, according to an embodiment of the present subject matter.

FIG. 19 is an illustration of a spatial arrangement of pixels in a sliding column used for the recursive calculation in vertical direction, according to an embodiment of the present subject matter.

FIG. 20A shows an input X-ray dental image. FIG. 20B shows an enhanced X-ray dental image of FIG. 20A. FIG. 20C shows another input X-ray dental image. FIG. 20D shows an enhanced X-ray dental image of FIG. 20C.

FIG. 23A shows an input. FIG. 23B shows an enhanced output image by CLAHE. FIG. 23C shows an enhanced output image by RSW-CLAHE. FIG. 23D shows another enhanced output image by RSW-CLAHE, using different parameter values. FIG. 23E shows an enhanced image by iterative RSW-CLAHE.

FIG. 24A shows an input. FIG. 24B shows an enhanced output image by CLAHE. FIG. 24C shows an enhanced output image by RSW-CLAHE. FIG. 24D shows another enhanced output image by RSW-CLAHE, using different parameter values. FIG. 24E shows an enhanced image by iterative RSW-CLAHE.

DETAILED DESCRIPTION

Figure 1:
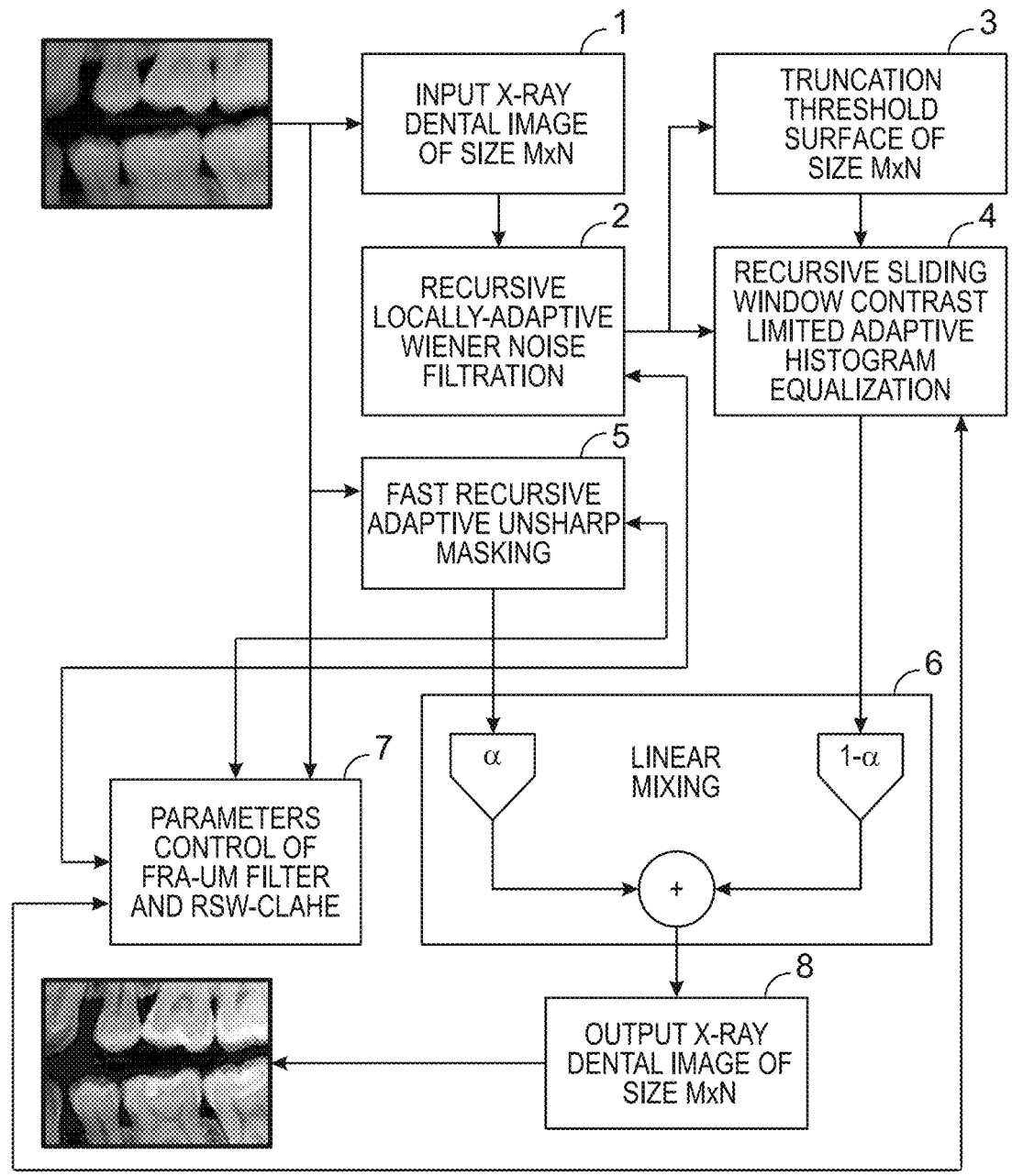
FIG. 1 is a block diagram illustrating performance of an X-ray dental image enhancement method, according to an embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

An example of a method and apparatus for enhancement the quality of medical images [1] uses unsharp masking filter and piecewise enhancement function to obtain the sharpened image. After that the image is rescaled, to eliminate the outliers and the contrast is enhanced through the known method of Contrast Limited Adaptive Histogram Equalization (CLAHE) [8]. The application of the method is illustrated through an X-ray chest image. In this example is not given quantitative evaluation of the improved medical images, compared to other similar methods.

An example of a method for enhancing radiographic images [2] includes suppressing of the structural noise, selecting a Region Of Interest (ROI) and increasing its contrast by applying CLAHE and interpolation of the enhanced image for its visualization, recording, or transmission. The results of the processing of X-ray images are presented, which include: increasing the contrast of the whole image, emphasizing only the ribs, contrasting only the selected ROI, and others. The characteristics of this class of images differ significantly from those of the X-ray dental images, which is why different approaches are used for their processing.

The basic methods for quality improvement of X-ray dental images could be classified as follows [3,4]: based on processing in the spatial domain, in the frequency domain, and through nonlinear (morphological) processing. Here are analyzed only methods for image processing in the spatial (pixel) domain, because the processing in the frequency domain requires the use of: direct and inverse 2D Fast Fourier Transform (2D-FFT), 2D Discrete Wavelet Transform (2D-DWT) or 2D Morphological Filtration (2D-MF) (the last one needs multiple recursive processing). Compared to the methods in the first group, the second group of methods require much higher computational resource, which limits the areas in which they can be applied.

The main methods in the first group (processing in the image spatial domain) could be generalized as follows:

1. Histogram Equalization (HE) [5] is a computer image processing technique used to improve contrast in images. It accomplishes this by effectively spreading out the most frequent intensity values, i.e., stretching out the intensity range of the image. This method usually increases the global contrast of the image when its usable data is represented by close contrast values. This allows for areas of lower local contrast to gain a higher contrast. Global Histogram Equalization (GHE) works well when the distribution of pixel values is similar throughout the image. However, when the image contains regions that are significantly lighter or darker than most of the image, the contrast in those regions will not be sufficiently enhanced.

2. Adaptive Histogram Equalization (AHE) [6] differs from the ordinary histogram equalization in respect that the adaptive method computes several histograms, each corresponding to a distinct section of the image, and uses them to redistribute the gray level of the image. AHE is therefore suitable for improving the local contrast and enhancing the definitions of edges in an image region. Sliding Window Adaptive Histogram Equalization (SWAHE) [7] improves on Histogram Equalization by transforming each pixel with a transformation function derived from a neighborhood region. However, SWAHE has the shortcoming of excessively amplifying noise, which may result in image distortion. SWAHE does not use a limitation of the maximum value of the local histogram in the sliding window. Thus, black pixels get even darker and white pixels get even whiter, and information can be lost.

3. Contrast Limited Adaptive Histogram Equalization (CLAHE) [8-11]—the contrast amplification in the vicinity of a given pixel value is given by the slope of the transformation function. This value is proportional to the slope of the neighborhood Cumulative Distributed Function (CDF) and therefore to the value of the histogram at that pixel value. CLAHE limits the amplification by clipping the histogram at a predefined value before computing the CDF. The clipping limit (CL)

defines the cutting-off level of the histogram and is a percent from its maximum. The coefficient CL is a real scalar in the range of [0,1]. The Default CL starts from 0.01 to 0.2.

However, in block based CLAHE, the contrast in the square tiles (contextual regions) will be different. The borders will contain errors because of the different contrasts in contextual regions. Bilinear Interpolation (BLI) is applied to resolve for this to the borders between the pixels so that the borders between the regions are not visible.

A major problem with using the CLAHE algorithm is the way to determine the optimal values of the CL parameters for each contextual region in the image. In [12] is proposed a learning-based parameters selection method for the CLAHE. The proposed supervised method was built and evaluated using contrast distortions from known image quality assessment datasets, containing over 6200 images with a large range of contrast and intensity variations. The disadvantage of this method is its significant computational complexity and the need to use an image database.

In [13] is applied Adaptive Enhancement of X-ray Images for contrast enhancement by CLAHE and morphological top and bottom hat operation for detail preservation capabilities. The disadvantage of this method is its high computational complexity.

In [14], a comparison of CLAHE with clip limit of 0.01 with the methods for histogram equalization, log transform and gamma correction for multiple gamma values with respect to the quality of X-ray dental periapical images, assessed by entropy criterion, was made. The results show that CLAHE maximizes the entropy in comparison with those algorithms. In the conclusion is claimed that the best enhancement is achieved by using the CLAHE method.

The clip limit CL will be determined at the point with maximum curvature on the entropy curve of the image [15]. However, to define the maximum curvature point, significant computational resource is needed.

4. One way to avoid the requirement of interpolation needed for the block based CLAHE is to use a sliding window approach instead [16]. In each step a histogram is created from a window around the pixel to be equalized. Only the center pixel is equalized and when sliding one pixel, the histogram can be incrementally updated, i.e. only the pixels in the sliding direction has to be added to the histogram and pixels behind removed. This approach makes it possible to skip the interpolation since windows are overlapping. Using a sliding window, the number of calculations for each window are fewer than for each tile in the block based version of CLAHE.

The disadvantage of this method is that a large number of arithmetic operations are required to calculate the parameter CL as a percentage of the maximum of the local histogram of the pixels in the sliding window for each of its positions in the image.

5. Specific for the X-ray dental image is that due to the process of its creation, the transitions are fuzzy. To improve the image quality are used algorithms, based on the linear Unsharp Masking (UM) technique [17, 18]. However, the transition enhancement through UM can result in the increasing of the noise level in the image. To avoid this, is used the algorithm Adaptive UM (AUM), used to detect the pixels placed on the transitions. In accordance with the method, for each of these pixels is executed transition enhancement, while on the remaining pixels is applied noise filtration.

One problem of the algorithm AUM is the growth of its computational complexity together with the size of the averaging sliding window used in the equation for sharpness enhancement. The size of the window is defined so that to frame the most frequent noise components which should be filtered.

6. The image contrast enhancement results in noise increasing in the processed X-ray dental images. Efficient methods for medical images denoising are known, based on the recurrent approach called Total Variation (TV) regularization, which needs large number of iterations [19].

One known method for noise reduction is the 2D Adaptive Wiener filter (2D-AWF) [20]. This filter is optimum, because in result is minimized the Mean Square Error (MSE), due to Gaussian white noise. The locally-adaptive 2D Wiener Filter (2D-WF) is more efficient than 2D-AWF [20]. One problem with the locally-adaptive Wiener filtration is the choice of the adaptation algorithm used to separate the pixels placed on the transitions from these in the homogenous areas of the image. The created filtration method is a combination of wavelet Wiener filter and adaptive weighted average spatial Wiener filter, and has high computational complexity.

In [21] a new method for optimal enhancement of the contrast of a medical image is proposed. The main idea is to improve the gamma correction to enhance the image information and the details based on the improved World Cup optimization (WCO) algorithm. This algorithm is used for optimal selection of the gamma value based on entropy criterion and edge content. The method needs at least 100 iterations which increases the execution time. The region of interest (ROI) in the processed images is manually classified by a dermatologist. No information is provided about dental images.

The present subject matter provides an improved process for X-ray dental imaging enhancement. In various embodiments, the process includes receiving an input image and applying contrast enhancement to the input image, including Recursive Locally-Adaptive Wiener Filtration (RLA-WF) of the noise and Recursive Sliding Window Contrast Limited Histogram Equalization (RSW-CLAHE) utilizing a Truncation Threshold Surface (TTS). The method also comprises applying sharpness enhancement to the input X-ray dental image, including using Fast Recursive Adaptive Unsharp Masking (FRA-UM) utilizing the sliding window, to obtain a sharpened image. The enhanced input image is linearly mixed with the sharpened input image using a control coefficient to obtain an output image, and the output image is provided to a display of a user, in various embodiments.

The present subject matter provides new method for X-ray dental image enhancement based on a sliding window moving one pixel at a time. This allows for the image enhancement to be adjusted more accurately based on the individual, smaller region characteristics.

FIG. 1 is a block diagram illustrating the performance of an X-ray dental image enhancement method, according to an embodiment of the present subject matter. In block 1 an X-ray dental image is obtained. According to the block diagram, the proposed method comprises: Recursive Locally-Adaptive Wiener Filtration (RLA-WF) for image de-noising (in block 2); Recursive Sliding Window Contrast Limited Adaptive Histogram Equalization (RSW-CLAHE) (in block 4) with individual threshold for each window position, based on Truncation Threshold Surface (TTS) (in block 3); Fast Recursive Adaptive Unsharp Masking (FRA-UM) (block 5) for edges enhancement and Linear Mixing (LM) (in block 6) for receiving of final enhanced image (in block 8)—combination between sharpened and contrasted image with reduced noise. In block 7, the parameters on which the operation of blocks 2, 4, 5 and 6 depends are controlled. The disclosures of each of these algorithms, and the connections between them are given below.

This Recursive Locally-Adaptive Wiener noise filtration (RLA-WF) algorithm is performed in block 2 of the scheme from FIG. 1. The filtration of the input image can be necessary because in the process of its formation on it is added a random noise generated by the X-rays conversion into electrical signals. In this case, the input noisy image is the matrix [X] of size M×N with pixels x(i,j) for i=1, 2, . . . , M and j=1, 2, . . . , N.

Figure 2:
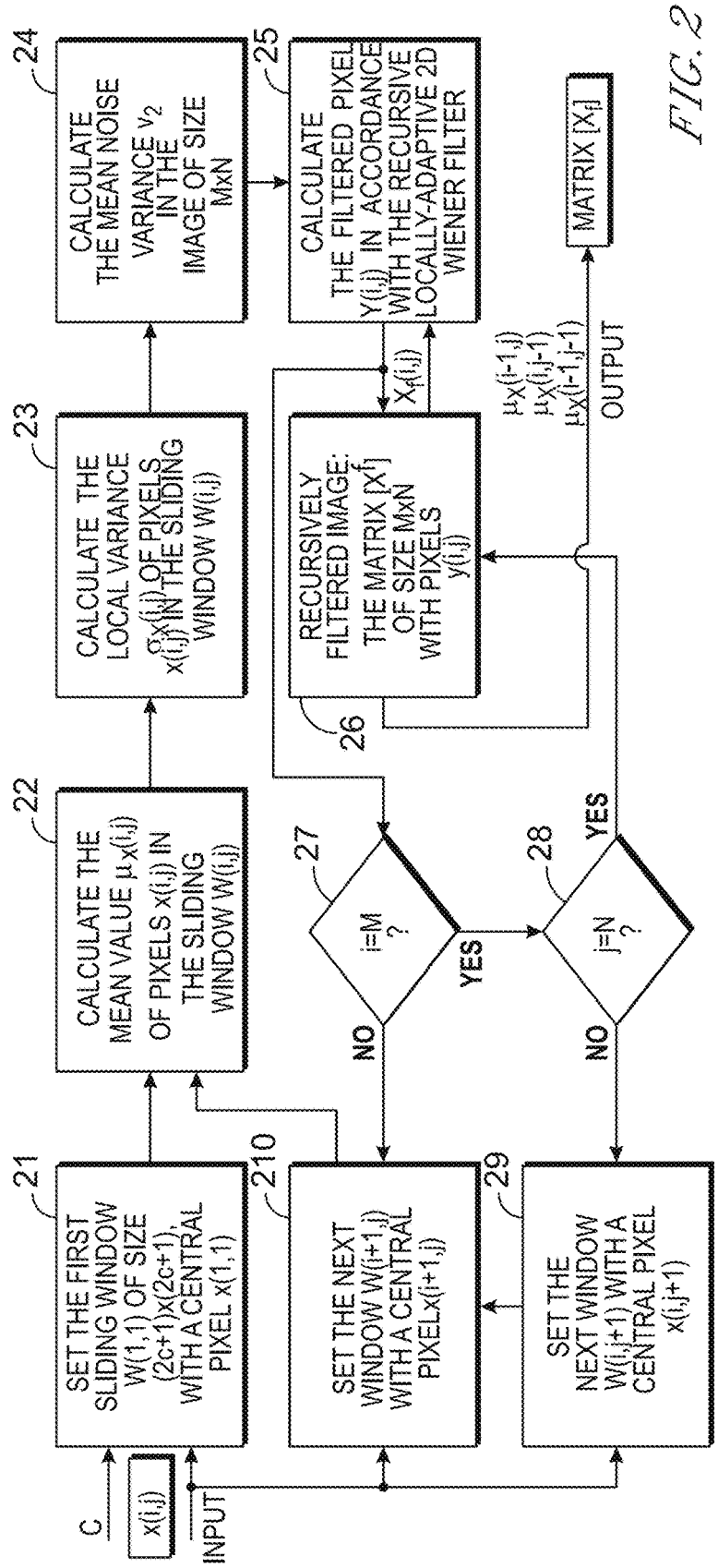
FIG. 2 is a block diagram illustrating an RLA-WF algorithm, according to an embodiment of the present subject matter.

FIG. 2 is a block diagram illustrating the RLA-WF algorithm, according to an embodiment of the present subject matter.

Figure 3:
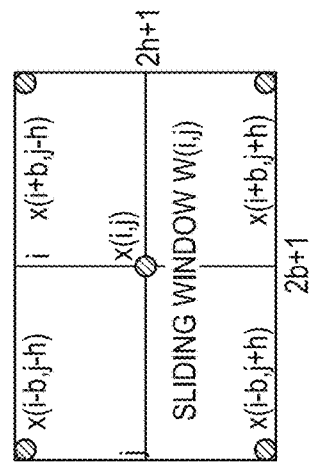
FIG. 3 is an illustration of a sliding window in a noisy input image, according to an embodiment of the present subject matter.

FIG. 3 is an illustration of a sliding window W(i,j) in the noisy input image with pixels x(i,j), according to an embodiment of the present subject matter. In accordance with the algorithm for locally-adaptive Wiener filtration is performed the lexicographic scan of the image matrix [X] through a sliding window W(i,j) of size (2b+1)×(2h+1), as shown in FIG. 3. The locally-adaptive image filtration for reduction of additive Gaussian noise is performed in block 25 in accordance with the relation:

$$x_f(i, j) = \begin{cases} \mu_x(i, j) + \frac{\sigma_x^2(i, j) - v^2}{\sigma_x^2(i, j)} [x(i, j) - \mu_x(i, j)] & \text{for } \sigma_x^2(i, j) \geq v^2; \\ \mu_x(i, j) & \text{for } \sigma_x^2(i, j) < v^2, \end{cases} \quad (1)$$

where $x_f(i,j)$—filtered input pixel x(i,j)

$$\mu_x(i, j) = (1/N_W) \sum_{m=-b}^{b} \sum_{n=-h}^{h} x(i+m, j+n)$$

mean value of the pixels x(i,j) in the sliding window W(i,j) of size (2b+1)×(2h+1); $N_W$=(2b+1)×(2h+1)—number of pixels in the sliding window W(i,j) (it is recommended to use a square window W(i,j) of size (2c+1)×(2c+1) for b=h=c); The value of $\mu_x(i,j)$ is calculated in block 22 of FIG. 2;

$$\sigma_x^2(i, j) = \left[ (1/N_W) \sum_{m=-b}^{b} \sum_{n=-h}^{h} x^2(i+m, j+n) \right] - \mu_x^2(i, j)$$

local variance of the pixels x(i,j) in the sliding window W(i,j). The value of $\sigma_x^2(i,j)$ is calculated in block 23;

$$v^2 = (1/M \times N) \sum_{i=1}^{M} \sum_{j=1}^{N} \sigma_x^2(i, j)$$

mean noise variance in the image [X] of size M×N. It is calculated in block 24.

For the acceleration of the calculation of the mean value $\mu_x(i,j)$ for each pixel except these on the first row and first column of the input matrix [X], are used recursive relations, executed in blocks 25 and 26:

$$\mu_x(i,j) = \mu_x(i-1,j) + \mu_x(i,j-1) - \mu_x(i-1,j-1) + (1/N_W)[x(i+b, j+h) - x(i+b,j-h-1) - x(i-b-1,j+h) + x(i-b-1,j-h-1)] \quad (2)$$

Figure 4:
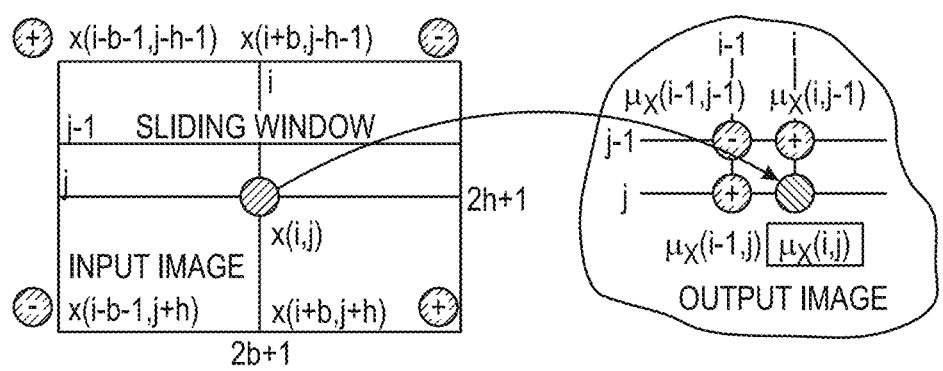
FIG. 4 is an illustration of a spatial arrangement of pixels used for a recursive calculation in a sliding window, according to an embodiment of the present subject matter.

FIG. 4 is an illustration of spatial arrangement of pixels used for the recursive calculation of the mean value $\mu_x(i,j)$ in a sliding window W(i,j) of size (2b+1)×(2h+1), according to an embodiment of the present subject matter. The spatial positions of the pixels which participate in equation (2) above are shown on FIG. 4.

As a result, the mean value $\mu_x(i,j)$ is recursively calculated by only 7 operations instead of performing addition of all pixels in the sliding window, where the needed operations are (2b+1)×(2h+1)−1 (for example, if b=h=5, then (2b+1)(2h+1)−1=120 and then the acceleration of the calculations of $\mu_x(i,j)$ is 120/7=17.14 times). This is the first advantage of the new approach, presented here. The second advantage of the offered RLA-WF compared to the known adaptive Wiener filtering [20], is that it is adaptive towards the level of the local variation compared to the global one, in result of which are retained the transitions in the image, while the noise is suppressed.

The Truncation Threshold Surface (TTS) algorithm is auxiliary and is used for the calculation of the truncation threshold for the local histogram in each sliding window. This algorithm is performed in bl. 3 of the scheme on FIG. 1.

Figures 5, 6:
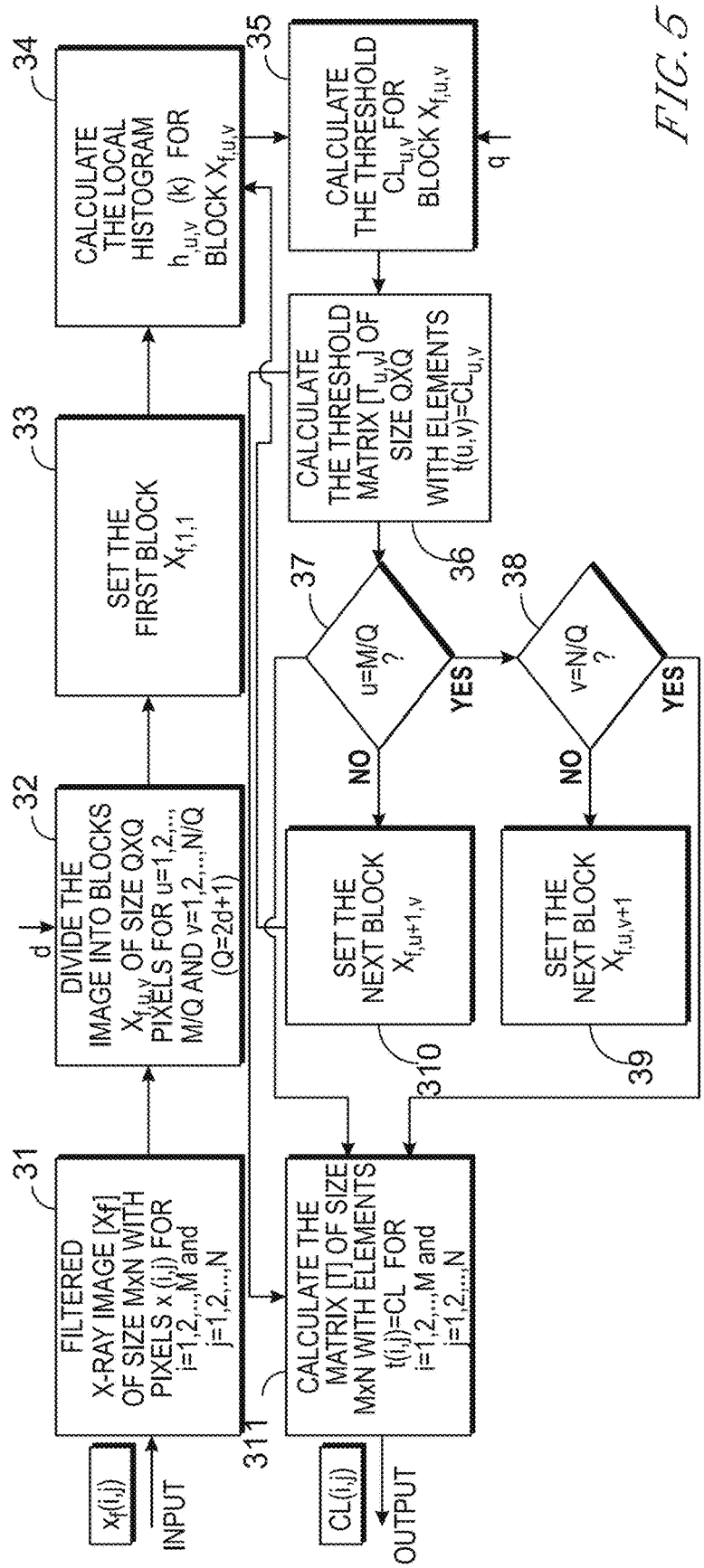
FIG. 5 is an illustration of an algorithm for calculation of Truncation Threshold Surface (TTS), according to an embodiment of the present subject matter.
FIG. 6 is an illustration of converting a pixel from an input image to a pixel of an output image by SW-CLAHE, according to an embodiment of the present subject matter.

FIG. 5 is a block diagram illustrating the TTS algorithm, according to an embodiment of the present subject matter. The matrix of the input filtered X-ray dental image $[X_f]$ (in bl. 31) is of size M×N pixels $x_f(i,j)$ for i=1, 2, . . . , M, j=1, 2, . . . , N and m—the number of grey levels per pixel (resp. u=$\log_2$ m—number of bits per pixel).

Step 1. In bl. 32, the image $[X_f]$ is divided into (MN)/Q² non-overlapping blocks $X_{f,u,v}$ of size Q×Q pixels each, for Q=2d+1 and u=1, 2, . . . , (M/Q) (number of blocks in horizontal direction), and v=1, 2, . . . , N/Q (number of blocks in vertical direction).

For each block $X_{f,u,v}$, obtained in blocks 33 and 310, is calculated the corresponding individual threshold $CL_{u,v}$ (in block 35) on the basis of the analysis of the local histogram $h_{u,v}(k)$ (in block 34) of this block.

$$CL_{u,v}(q) = q \times \max\{h_{u,v}(k)\} = q \times \max\{n_{u,v}(k)/Q^2\} \text{ for } k=0,1,2,\ldots,m-1, \quad (3)$$

where $$n_{u,v}(k) = \sum_{p=-d}^{d} \sum_{s=-d}^{d} 1_{x_f(i+p,j+s)=k}$$

is the number of pixels in the level k of the block $X_{f,u,v}$; q—truncation coefficient for the maximum value of each histogram $h_{u,v}(k)$ for u=1, 2, . . . , (M/Q) and v=1, 2, . . . , N/Q. The value of q is chosen in the range 0.00001≤q≤0.2 on the basis of the quality metrics of the processed image.

An alternative to (3) algorithm for determining the adaptive threshold $CL_{u,v}^{adap}$ is proposed, the value of which does not depend on the parameter q, but on the distribution of the local histogram $h_{u,v}(k)$ of the block $X_{f,u,v}$. According to this algorithm, the threshold $CL_{u,v}^{adap}$ is calculated so that the histogram $h_{u,v}(k)$ to divide in 2 parts of the same area with a value of 0.5. As a result of the application of SW-CLAHE with adaptive threshold, maximum contrast of the central pixel of the block $X_{f,u,v}$ is provided due to the maximum linear stretching of its histogram without loss of gray levels.

The calculation of the value of the adaptive threshold $CL_{u,v}^{adap}$ is performed using the following recursive iterative algorithm:
1. Calculation of CLP for initial image block $X_{f,u,v}$ for u=v=0:
Let $CL_{u,v}^{adap}=x$ with initial values x=0 and δ=0.01.

and SW-CLAHE with threshold $CL_{u,v}$ for fixed value of the parameter q.

For the example of FIG. 6 in Table 1 are presented all iterative steps for calculating the adaptive threshold $CL_{u,v}^{adap}$ with initial value x=0 (for u=v=0) in accordance with algorithm (4).

TABLE 1

Description of the iterative calculation of $CL_{i,j}^{adap}$ = x = 0.08 for S(x) = 0.48

| $h_{u,v}(k)$ | x = 0.01 | x = 0.02 | x = 0.03 | x = 0.04 | x = 0.05 | x = 0.06 | x = 0.07 | x = 0.08 |
|---|---|---|---|---|---|---|---|---|
| 0.12 | 0.11 | 0.10 | 0.09 | 0.08 | 0.07 | 0.06 | 0.05 | 0.04 |
| 0.24 | 0.23 | 0.22 | 0.21 | 0.20 | 0.19 | 0.18 | 0.17 | 0.16 |
| 0.16 | 0.15 | 0.14 | 0.13 | 0.12 | 0.11 | 0.10 | 0.09 | 0.08 |
| 0.20 | 0.19 | 0.18 | 0.17 | 0.16 | 0.15 | 0.14 | 0.13 | 0.12 |
| 0.16 | 0.15 | 0.14 | 0.13 | 0.12 | 0.11 | 0.10 | 0.09 | 0.08 |
| 0.08 | 0.07 | 0.06 | 0.05 | 0.04 | 0.03 | 0.02 | 0.01 | 0.00 |
| 0.04 | 0.03 | 0.02 | 0.01 | 0.00 | 0.00 | 0.00 | 0.00 | 0.00 |
| 0.00 | 0.00 | 0.00 | 0.00 | 0.00 | 0.00 | 0.00 | 0.00 | 0.00 |
| S = 1.00 | S = 0.93 | S = 0.86 | S = 0.79 | S = 0.72 | S = 0.66 | S = 0.60 | S = 0.54 | S = 0.48 |

$$\text{St. 1. } x = x + \delta; \quad (4)$$

$$\text{St. 2. } S_{u,v}(x) \sum_{k=0}^{m-1} [h_{u,v}(k) - x] \text{ for } h_{u,v}(k) \geq x;$$

$$\text{St. 3. If } S_{u,v}(x) = \begin{cases} > 0.5\text{-return in step 1,} \\ \approx 0.5\text{-go to step 4;} \end{cases}$$

$$\text{St. 4. Stop and } CL_{u,v}^{adap} = X,$$

where $h_{u,v}(k)$ is the local histogram of the pixels in the block $X_{f,u,v}$; m—number of pixels gray level.

2. Recursive calculation of $CL_{u+1,v}^{adap}$ for next neighbor image block, for example $X_{f,u+1,v}$, with local histogram $h_{u+1,v}(k)$:
Initial value for $CL_{u+1,v}^{adap}=CL_{u,v}^{adap}=x$.
St. 1. Calculation of $$S_{u+1,v}(x) = \sum_{k=0}^{m-1} [h_{u+1,v}(k) - x];$$

St. 2. Check of the conditions:
if $S_{u+1,v}(x) \approx 0.5$ go to step 3;
if $S_{u+1,v}(x) > 0.5$, then x=x+δ and go to step 1;
if $S_{u+1,v}(x) < 0.5$, then x=x−δ and go to step 1;
St. 3. Stop and $CL_{u+1,v}^{adap}=x$.

Depending on the position (u,v) of the current block $X_{f,u,v}$, image size M×N and the selected way of scanning the image blocks (scan type for example: progressive, meander, Peano-Hilbert, etc.) next neighboring block can be not only $X_{f,u+1,v}$, but also one of the blocks $X_{f,u,v+1}$ or $X_{f,u+1,v+1}$.

The recursive calculation of CL leads to its acceleration, which is due to the big correlation between the spatially adjacent blocks of the image. For this reason, the number of iterations required to calculate the CL for each block except the initial one is reduced.

FIG. 6 is an illustration of an example for converting the pixel x(i,j)=3 from the input image to the pixel g(i,j)=4 of the output image with m=8 gray levels via SW-CLAHE, according to an embodiment of the present subject matter. The example shows the contrast conversion of the central pixel x(i,j)=3 of a block with sizes 5×5 pixels using algorithms HE From the analysis of the histogram $h_{u,v}(k)$ for the example of FIG. 6 it follows that for k=1, $h_{max}(k)=0.24$. If we assume q=0.2 from expression (3) we get:

$$CL_{u,v}(q)=0.2\times0.24=0.05.$$

This value of $CL_{u,v}$ is used in the non-iterative algorithm SW-CLAHE with a fixed value of q.

The choice of algorithm for calculating the threshold $CL_{u,v}$ is determined by the requirements of the specific application of SW-CLAHE: for visual evaluation of a tooth image of a given type or for automatic analysis, for example by an artificial intelligence system based on neural networks.

Step 2. Calculation in block 311 of the truncation thresholds surface–matrix [T] of size M×N, comprising the blocks $T_{u,v} \equiv X_{f,u,v}$. In the space, defined by the centers of each four spatially-neighboring blocks $T_{u,v}$, $T_{u+1,v}$, $T_{u,v+1}$, $T_{u+1,v+1}$, is defined the matrix $[T_{u,v}]$ of size Q×Q with elements $t_{u,v}(\alpha,\beta)$ for α,β=0, 1, . . . , Q−1.

Figure 7:
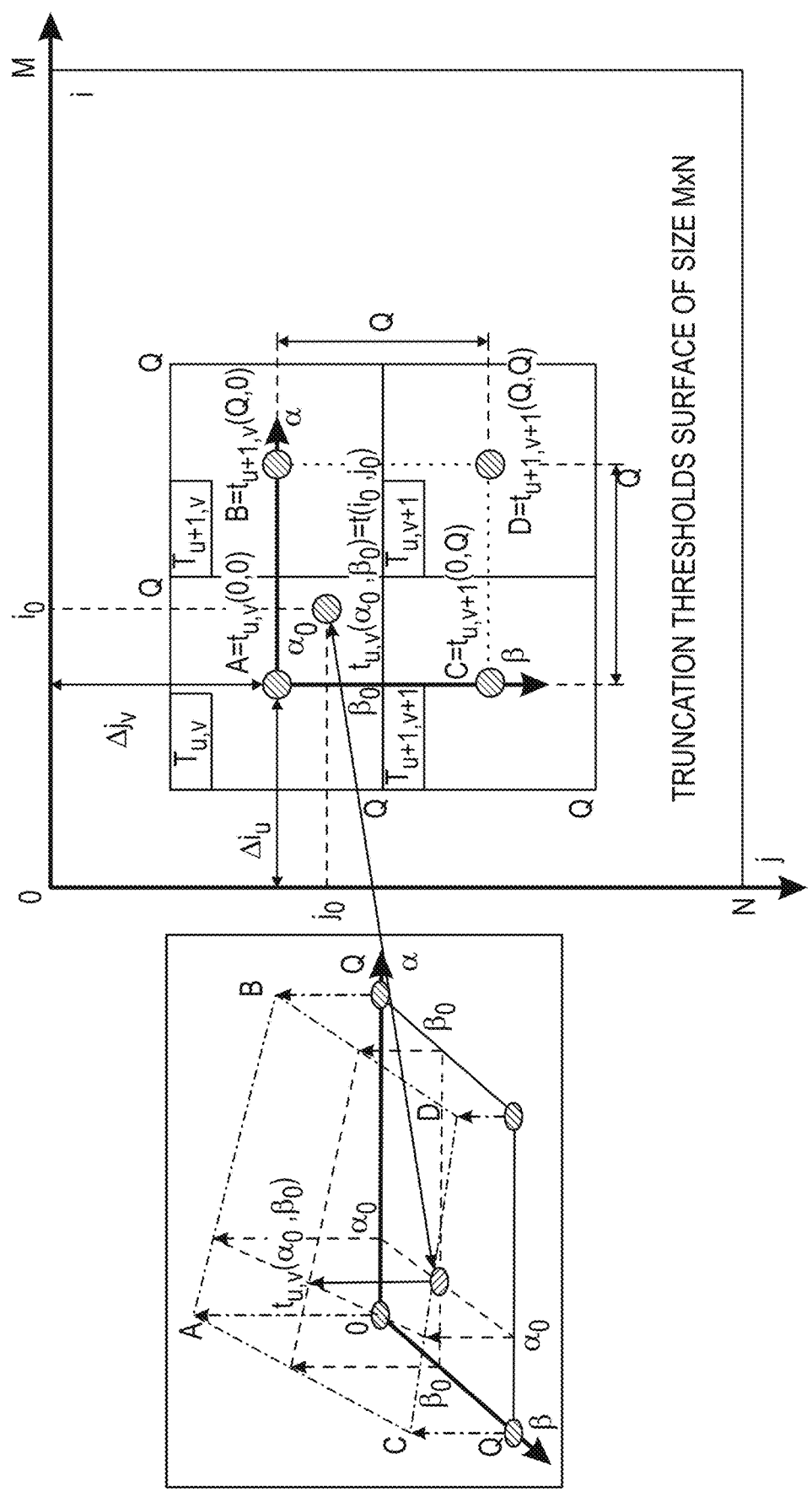
FIG. 7 is an illustration of a calculation of the TTS by bilinear interpolation, according to an embodiment of the present subject matter.

FIG. 7 is an illustration of calculation of the TTS (a matrix [T] of size M×N) by bilinear interpolation, according to an embodiment of the present subject matter. The following symbols were accepted for the corner elements of the matrix $[T_{u,v}]$, resp.: $t_{u,v}(0,0)=A$, $t_{u+1,v}(Q,0)=B$, $t_{u,v+1}(0,Q)=C$, $t_{u+1,v+1}(Q,Q)=D$, as shown in FIG. 7. In this case, A, B, C and D coincide with the thresholds $CL_{u,v}$, $CL_{u+1,v}$, $CL_{u,v+1}$, $CL_{u+1,v+1}$ for the group of our spatially-neighboring blocks $T_{u,v}$, $T_{u+1,v}$, $T_{u,v+1}$, $T_{u+1,v+1}$.

The remaining elements $t_{u,v}(\alpha,\beta)$ of the matrix $[T_{u,v}]$ are calculated in bl. 36 through BLI (Bilinear Interpolation) in correspondence with the relation:

$$t_{u,v}(\alpha_0,\beta_0)=(1/Q^2)[A(Q-\alpha_0)(Q-\beta_0)+\beta_0 C(Q-\alpha_0)+\alpha_0 B(Q-\beta_0)+\alpha_0\beta_0 D] \quad (6)$$

for $\alpha_0$, $\beta_0=0, 1, \ldots Q-1$. Here $(\alpha_0,\beta_0)$ are the local coordinates of the element $t_{u,v}(\alpha_0,\beta_0)$ of the matrix $[T_{u,v}]=[t_{u,v}(\alpha_0,\beta_0)]$.

To define the threshold $CL_{i,j}$ for the histogram truncation in the window W(i,j) for the pixel x(i,j) in the global coordinate system (i,j) for i=0, 1, . . . , M−1 and j=0, 1, . . . , N−1, is necessary to take into account the displacement $(\Delta i_u, \Delta j_v)$ of the origin of the local coordinate system of the block, related to the original. Then the needed local threshold $CL_{u,v}(i,j)$ (calculated in a block 311) for the pixel $x_f(i,j)$ from the block $T_{u,v}$, is defined by the relation:

$$CL_{u,v}(i,j)=t_{u,v}(\Delta i_u+\alpha,\Delta j_v+\beta)=t_{u,v}(i,j) \quad (7)$$

for $u=1, 2, \ldots, (M/Q; v=1, 2, \ldots, (N/Q); i=0, 1, \ldots, M-1; j=0, 1, \ldots, N-1;$
$\Delta i_u=0, Q, 2Q, \ldots, (M/Q)-1; \Delta j_v=0, Q, 2Q, \ldots, (N/Q)-1.$ The so presented algorithm for the definition of $CL_{u,v}(i,j)$ is executed before the SW-CLAHE algorithm. To simplify the explanations, in the description below the indices u,v of the local threshold $CL(i,j)$, and respectively—of the element $t(i,j)$ of the matrix [T] will not be used, because they are a function only of the variables (i,j).

Figure 8:
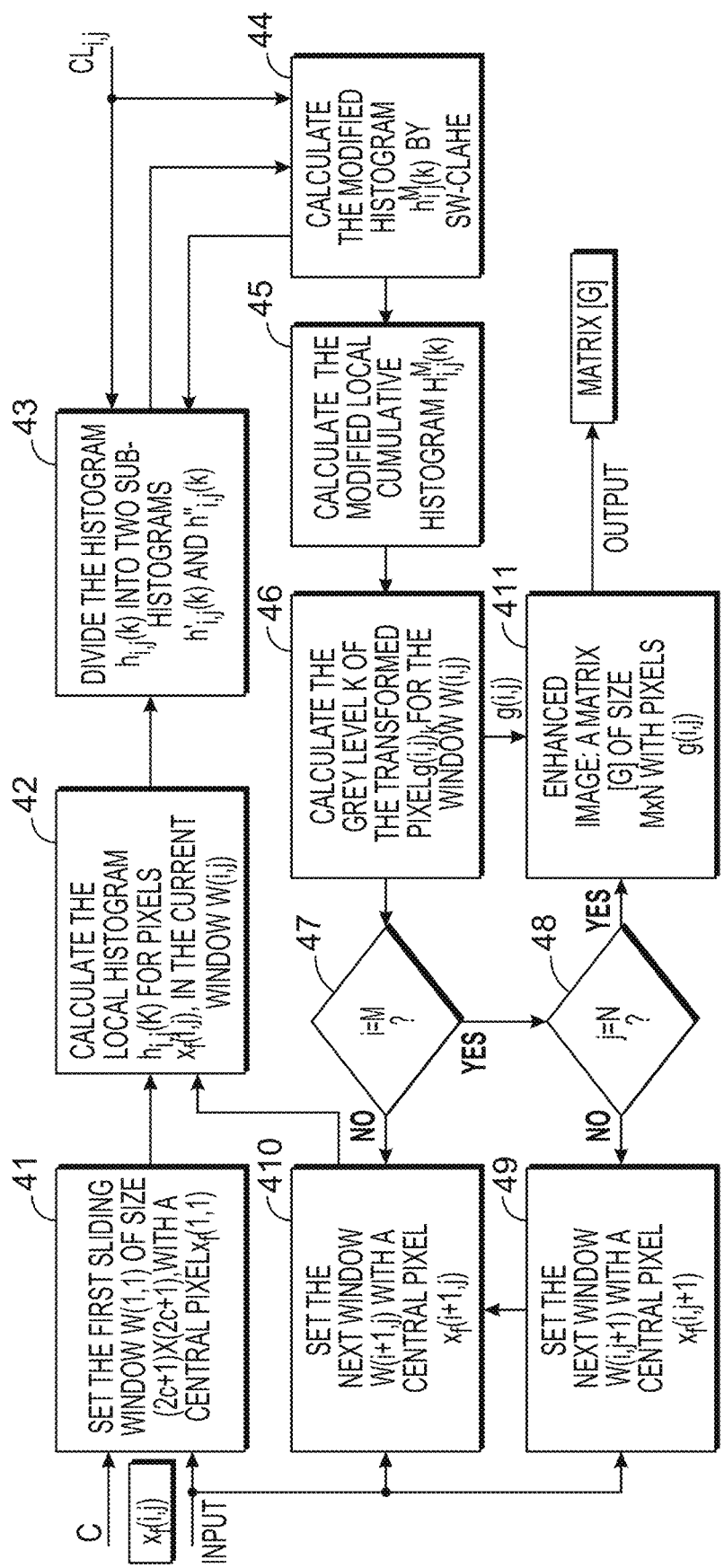
FIG. 8 is a block diagram illustrating an RSW-CLAHE algorithm, according to an embodiment of the present subject matter.

The Recursive Sliding Window Contrast Limited Adaptive Histogram Equalization (RSW-CLAHE) algorithm is performed in block 4 of the scheme on FIG. 1. This algorithm is designed to enhance local contrast of each pixel of the input image based on the pixels in the sliding window that it covers. FIG. 8 is a block diagram illustrating the RSW-CLAHE algorithm, according to an embodiment of the present subject matter.

Step 1. The local histogram $h_{i,j}(k)$ is calculated in block 42 for the pixels in the sliding window $W(i,j)$ whose central pixel is $x(i,j)$:

$$h_{i,j}(k)=n_{i,j}(k)/N_W \text{ for } k=0,1,2,\ldots,m-1. \quad (8)$$

Figure 9:
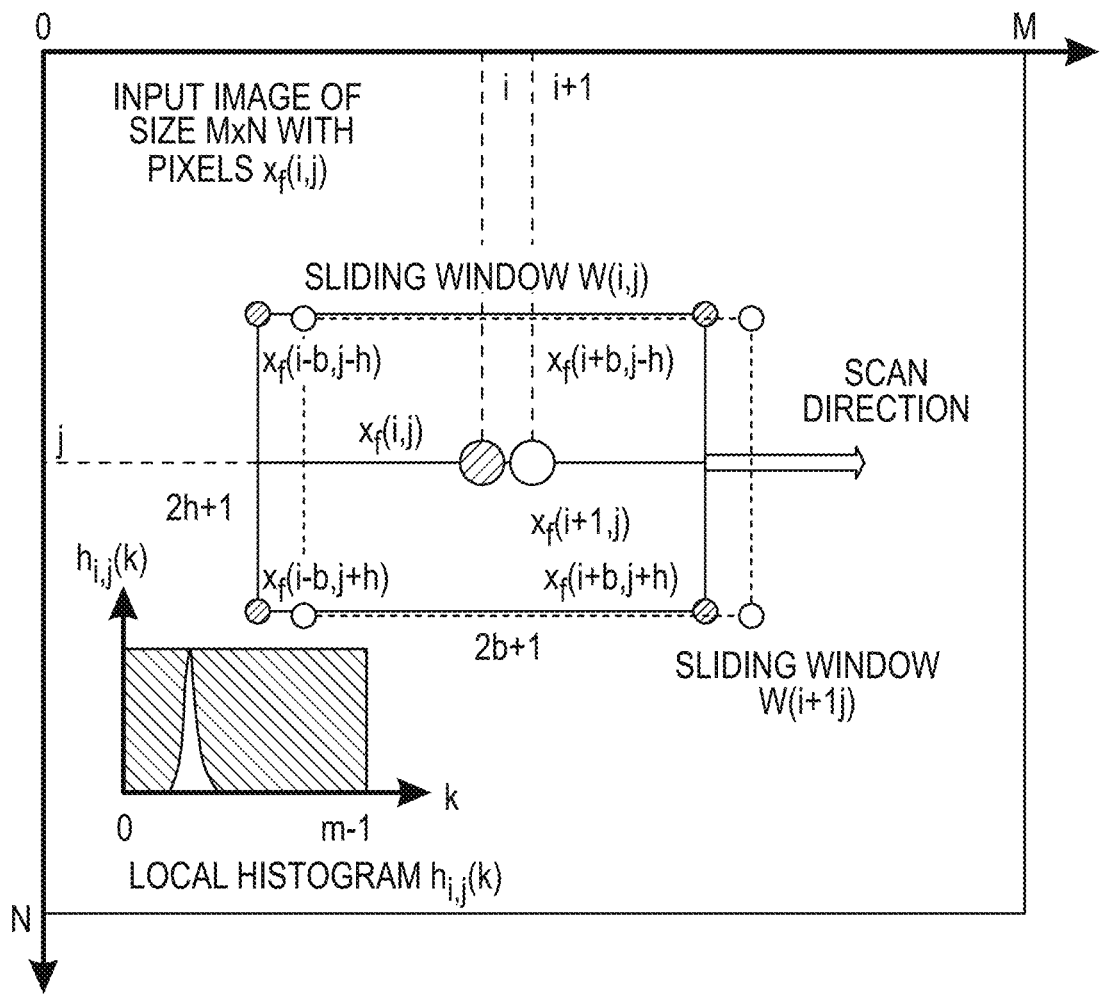
FIG. 9 is an illustration of two consecutive positions of a sliding window, according to an embodiment of the present subject matter.

Here $N_W=(2b+1)(2h+1)$ is the number of pixels in the sliding window $W(i,j)$ of size $(2b+1)\times(2h+1)$ whose center coincides with the pixel $x_f(i,j)$ (it is recommended to use a square window $W(i,j)$ of size $(2c+1)\times(2c+1)$ for b=h=c);

$$n_{i,j}(k) = \sum_{p=-b}^{b}\sum_{s=-h}^{h} 1_{x_f(i+p,j+s)=k}$$

the number of pixels with grey level k in the sliding window $W(i,j)$, as shown in FIG. 9, which is an illustration of two consecutive positions of the sliding window $W(i,j)$ and $W(i+1,j)$, according to an embodiment of the present subject matter.

Step 2. The values of the local histogram $h_{i,j}(k)$ are separated into two parts (in block 43) by the individual threshold, $CL_{i,j}$. The parts of the histogram are calculated in correspondence with the relations:

$$h'_{i,j}(k) = \begin{cases} h_{i,j}(k) - CL_{i,j} & \text{for } h_{i,j}(k) \geq CL_{i,j}; \\ 0 & \text{for } h_{i,j}(k) < CL_{i,j}; \end{cases} \quad (9)$$

$$h''_{i,j}(k) = \begin{cases} CL_{ij} & \text{for } h_{i,j}(k) \geq CL_{i,j}, \\ h_{i,j}(k) & \text{for } h_{i,j}(k) CL_{i,j}. \end{cases}$$

In this case $h'_{i,j}(k)+h''_{i,j}(k)=h_{i,j}(k)$. The value of the threshold $CL_{i,j}$ is in the range $0<CL_{i,j}<1$ and is calculated before the execution of the BLI algorithm.

Figure 10:
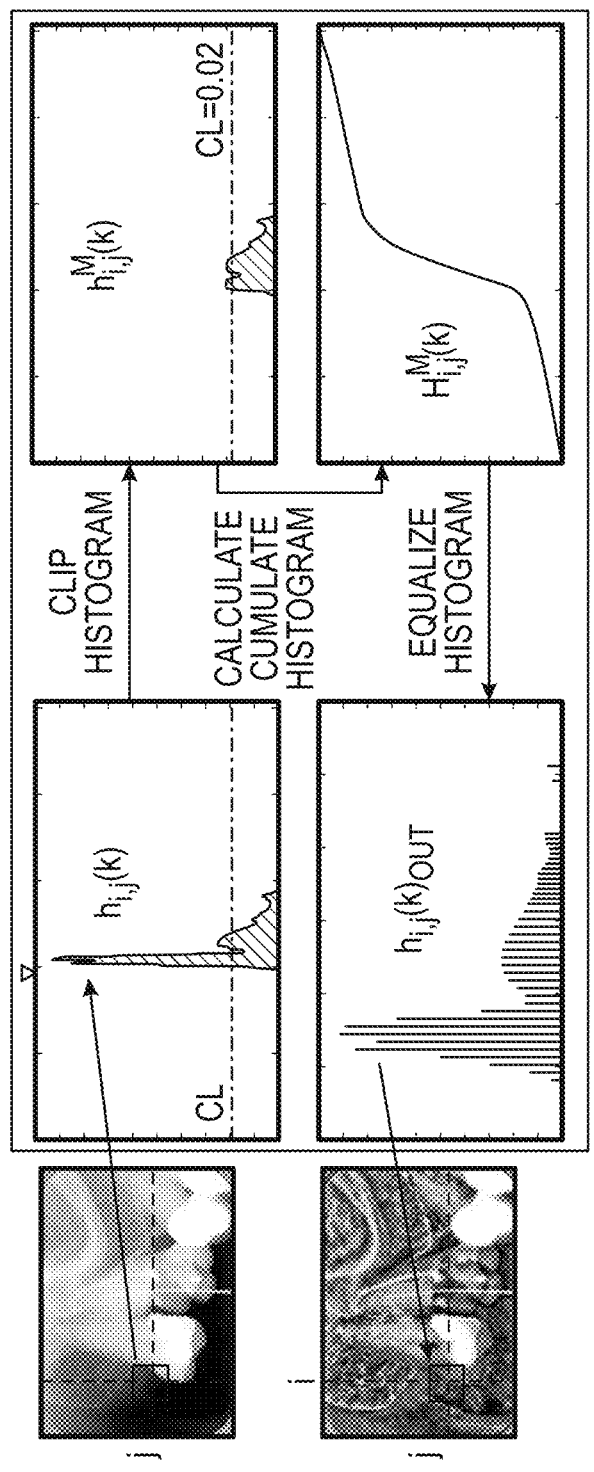
FIG. 10 is a graphical representation of RSW-CLAHE for a current window, according to an embodiment of the present subject matter.
Figure 11:
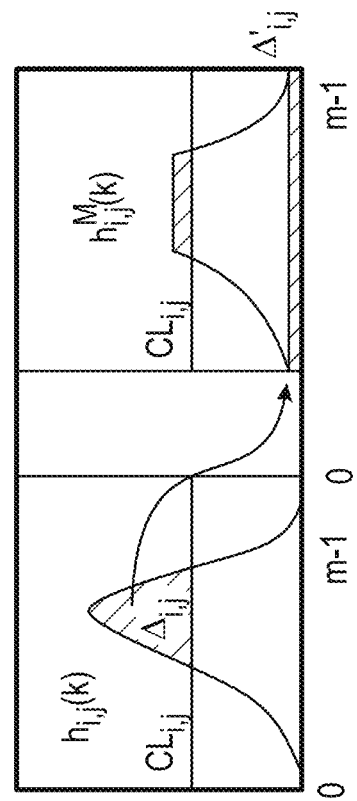
FIG. 11 is an illustration of setting the value of a threshold for a local histogram, according to an embodiment of the present subject matter.

Step 3. Calculation of the modified local histogram $h_{i,j}^M$ (k) in block 44 for the sliding window $W(i,j)$ in correspondence with the SW-CLAHE algorithm, shown on FIG. 10, which is a graphical representation of RSW-CLAHE for the current window, according to an embodiment of the present subject matter.

$$h_{i,j}^M(k) = (\Delta_{i,j}/m) + h''_{i,j} = (1/m)\sum_{k=0}^{m-1} h'_{i,j}(k) + h''_{i,j}(k), \quad (10)$$

where $$\Delta'_{i,j} = \Delta_{i,j}/m = (1/m)\sum_{l=0}^{m-1} h'_{i,j}(l)$$

is the basic level of the modified local histogram $h_{i,j}^M(k)$ as shown in FIG. 11, which is an illustration of setting the value of the threshold $CL_{i,j}$ for the local histogram $h_{i,j}(k)$, according to an embodiment of the present subject matter.

Step 4. Calculation of the modified local cumulative histogram $H_{i,j}^M(k)$ in block 45 for the pixel (i,j):

$$H_{i,j}^M(k) = \sum_{l=0}^{k} h_{i,j}^M(l) = [(k+1)/m]\sum_{l=0}^{m-l} h'_{i,j}(l) + \sum_{l=0}^{k} h''_{i,j}(l) \text{ for } k = 0,$$

$$1, 2, \ldots, m-1. \quad (11)$$

Step 5. Calculation of the new grey level $g_k(i,j)$ of 10 bits in block 46 of the pixel (i,j) from the enhanced image, which replaces the grey level value k of the 8 bits/pixel $x_f(i,j)$ from the input filtered image, and is placed in the center of the sliding window $W(i,j)$:

$$g_k(i,j) = \begin{cases} m-1 & \text{for } \lfloor (m-1)H_{i,j}^M(k) + 0.5 \rfloor m-1; \\ \lfloor (m-1)H_{i,j}^M(k) + 0.5 \rfloor & \text{-in all other cases.} \end{cases} \quad (12)$$

In result is obtained the modified image with pixels $g_k(i,j)$, whose truncated histogram is equalized. By increasing the number of bits per pixel of the image with improved contrast, the appearance of false contours in areas with the same levels of gray is avoided. In the description below, the index k for the grey level of the pixel g(i,j) will not be used, because it depends only of the variables (i,j).

Figure 12:
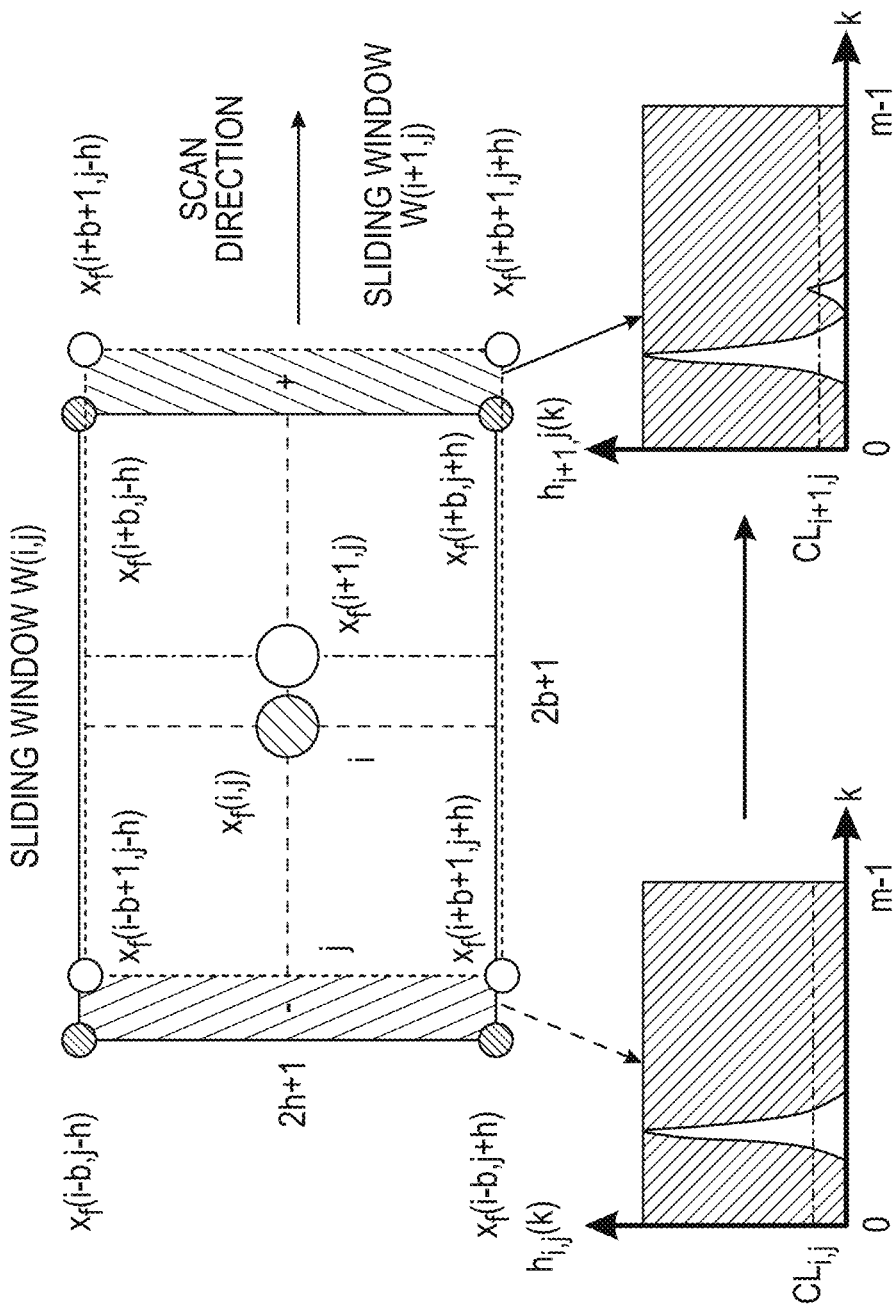
FIG. 12 is an illustration of a recursive calculation of a histogram, according to an embodiment of the present subject matter.

Step 6. The sliding window $W(i,j)$ is moved one position ahead in horizontal direction, so that its center to coincide with the pixel $x(i+1,j)$. For the new position of the window $W(i+1,j)$ is calculated in block 44 recursively the corresponding local modified histogram $h_{i+1,j}^M(k)$ shown in FIG. 12, which is an illustration of recursive calculation of the histogram $h_{i+1,j}^M(k)$ based on $h_{i,j}^M(k)$, according to an embodiment of the present subject matter:

$$h_{i+1,j}^M(k)=h_{i,j}^M(k)-h_{i+b,j}^M(k)+h_{i+b+1,j}^M(k) \text{ for } k=0,1,$$
$$2,\ldots,m-1, \quad (13)$$

where $h_{i-b,j}^M(k)$ and $h_{i+b+1,j}^M(k)$ are respectively the modified histograms with grey level k in the first column (i−b) of the window $W(i,j)$ with center (i,j), and in the last column (i−b+1) of the window $(i+1,j)$ with center $(i+1,j)$. Here $CL_{i+1,j}$ is the value of the threshold for the histogram of the pixels in the window with center $x_f(i+1,j)$.

The modified histogram for the first column (i−b) of the window $W(i,j)$ is:

$$h_{i-b,j}^M(k) = \begin{cases} \Delta'_{i,j} h_{i-bj}^{(k)} & \text{for } h_{i-b,j}(k) < CL_{i,j}; \\ \Delta'_{i,j} & \text{for } h_{i-b,j}(k) \geq CL_{i,j}, \end{cases} \quad (14)$$

where $$h_{i-b,j}(k) = n_{i-b,j}(k)/(2h+1) \text{ for } n_{i-b,j}(k) = \sum_{s=-h}^{h} 1_{x_f(i-b,j+s)=k};$$

$$\Delta'_{i,j} = (1/m) \sum_{l=0}^{m-2} h'_{i,j}(l);$$

$$h''_{i-b,j}(k) = \begin{cases} h_{i-b,j}(k) & \text{for } h_{i-b,j}(k) < CL_{i,j}; \\ CL_{i,j} & \text{for } h_{i-b,j}(k) \geq CL_{i,j}. \end{cases}$$

The modified histogram for the last column (i+b+1) of the window W(i+1,j) is:

$$h^M_{i+b+1,j}(k) = \begin{cases} \Delta'_{i+1,j} + h''_{i+b+1,j}(k) & \text{for } h_{i+b+1,j}(k) < CL_{i+1,j}; \\ \Delta'_{i+1,j} & \text{for } h_{i+b+1,j}(k) \geq CL_{i+1,j}, \end{cases} \quad (15)$$

where $$h_{i+b+1,j}(k) = n_{i+b+1,j}(k)/(2h+1) \text{ for}$$

$$n_{i+b+1,j}(k) = \sum_{s=-h}^{h} 1_{x_f(i+b+1,j+s)=k};$$

$$\Delta'_{i+1,j} = (1/m) \sum_{l=0}^{m-1} h'_{i+1,j}(l);$$

$$h''_{i+b+1,j}(k) = \begin{cases} h_{i+b+1,j}(k) & \text{for } h_{i+b+1,j}(k) < CL_{i+1,j}; \\ CL_{i,j} & \text{for } h_{i+b+1,j}(k) \geq CL_{i+1,j}, \end{cases}$$

Step 7. For each next window position when i=b+2, b+3, . . . , M−b and j=h+2, h+3, . . . , N−h, the steps 3-6 are executed again in blocks 47 and 48. The initial position of the window is defined by the pixel $x_f$(b+1,h+1) in bl. 41, and the window moves to the next position from left to right (in bl. 49) and to the next row below (in block 410).

Unlike the known CLAHE algorithm, the offered here algorithm RSW-CLAHE is using a sliding window placed around each pixel, whose histogram has an individual clipping factor, CL based on the TTS. The calculation of the local modified histogram is accelerated through a recursion.

For the example of FIG. 6 are built respectively local histograms h(k) and H(k) on the basis of which Histogram Equalization (HE) is performed. In this case, the pixel x(i,j)=3 is transformed according to the HE algorithm:

$$g_{k=3}(i,j) = \lfloor 7H_{i,j}(3) + 0.5 \rfloor = \lfloor 7 \times 0.72 + 0.5 \rfloor = 5.$$

Figure 13:
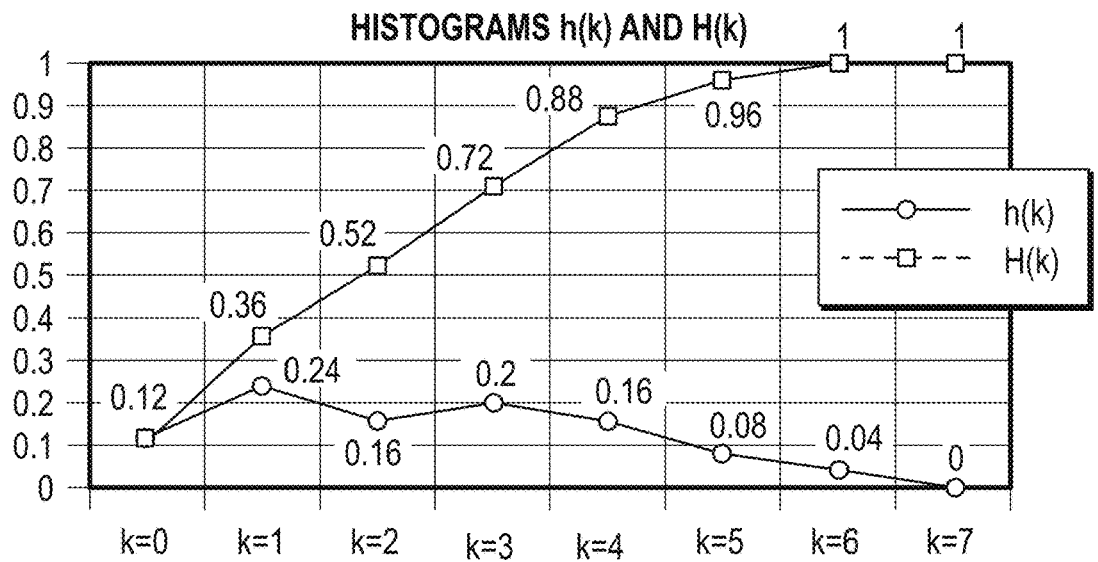
FIG. 13 is an illustration of local histograms for execution of Histogram Equalization, according to an embodiment of the present subject matter.

FIG. 13 is an illustration of an example for the local histograms h(k) and H(k) for execution of HE, according to an embodiment of the present subject matter.

Figure 14:
FIG. 14 is an illustration of histograms for non-iterative SW-CLAHE and iterative SW-CLAHE, according to an embodiment of the present subject matter.
Figure 14:
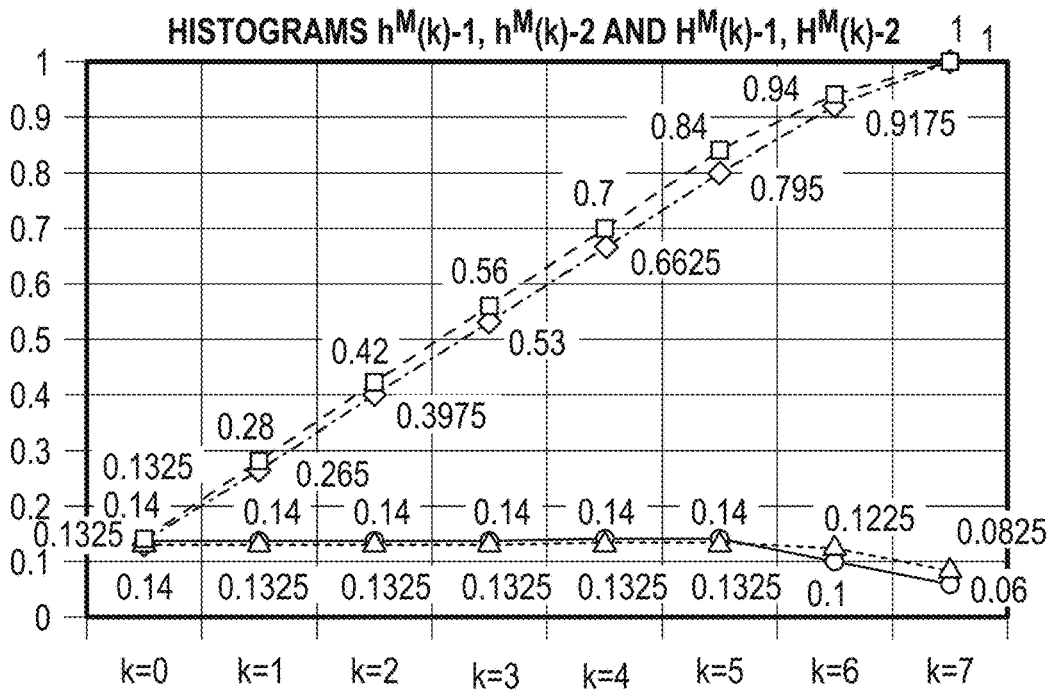

FIG. 14 is an illustration of histograms $h^M(k)$−1, $H^M(k)$−1 and $h^M(k)$−2, $H^M(k)$−2, respectively, for non-iterative SW-CLAHE-1 and iterative SW-CLAHE-2, according to an embodiment of the present subject matter. In FIG. 14 for the same example of FIG. 13 are given the corresponding local histograms $h^M(k)$ and $H^M(k)$ with index 1 for the non-iterative, and with index 2—for the iterative SW-CLAHE. After applying the corresponding algorithm:

$$g_{k=3}^M(i,j) = \lfloor 7H_{i,j}^M(3) + 0.5 \rfloor = \lfloor 7 \times 0.53 + 0.5 \rfloor = 4 \text{ for non-iterative SW-CLAHE-1}$$

$$g_{k=3}^M(i,j) = \lfloor 7H_{i,j}^M(3) + 0.5 \rfloor = \lfloor 7 \times 0.56 + 0.5 \rfloor = 4 \text{ for iterative SW-CLAHE-2}$$

The graphics of FIG. 13 for the corresponding pairs of histograms with indices 1 and 2 show their great proximity and better linearity compared to those in FIG. 14.

Conclusions from the analysis of the results presented in FIGS. 13 and 14:

As a result of the application of the new iterative algorithm for the adaptive CL calculation, the modified local histogram $h^M(k)$−2 is equalized very good. The corresponding modified cumulative local histogram $H^M(k)$−2 is linear in the region where $h^M(k)$−2=const. Thus, the contrast of the original image is increased as a result of linear stretching of its histogram. The comparison of graphics H(k) and $H^M(k)$−2 shows that for HE in the graphic H(k) is reached a saturation (which means that part of the grey levels in the processed image are lost), while in the iterative calculation of CL there is no loss of gray levels.

According to the proposed iterative algorithm, the value of CL takes into account the distribution of the whole local histogram, while according to the non-iterative algorithm, CL is determined only by the maximum value of the local histogram within the sliding window.

Compared to the non-iterative SW-CLAHE algorithm with fixed value of q, the new iterative algorithm does not require setting the value of q, because this parameter is not used for the adaptive calculation of the CL.

The Fast Recursive Adaptive Unsharp Masking (FRA-UM) algorithm is executed in block 5 of the scheme of FIG. 1. It is designed to increase the sharpness of the input X-ray image [X] without decreasing the steepness of the transitions. Instead of the known Unsharp Masking algorithm, a new recursive adaptive UM algorithm is applied here, which significantly speeds up its execution.

Figure 15:
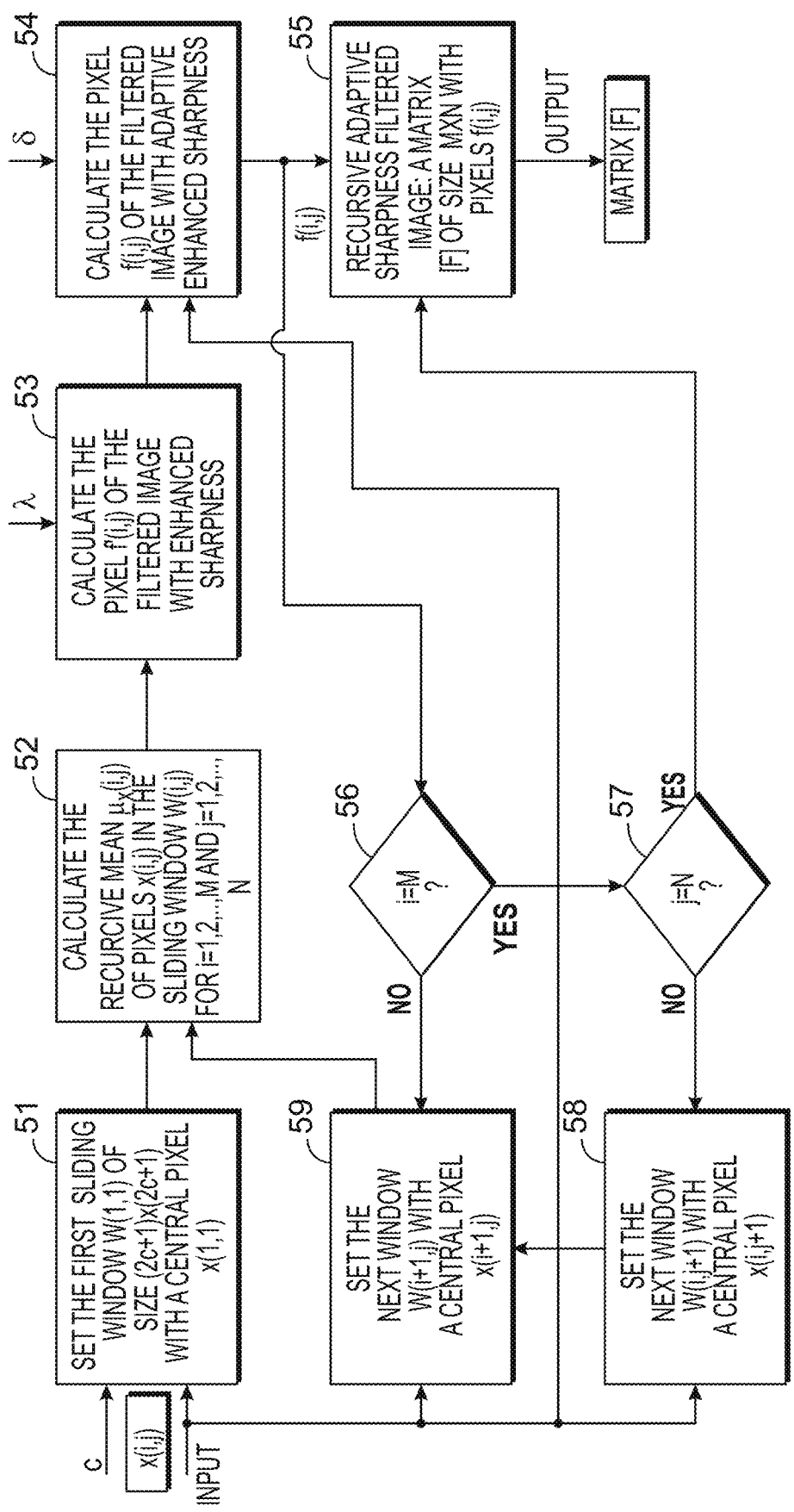
FIG. 15 is a block diagram of an FRA-UM algorithm, according to an embodiment of the present subject matter.

The FRA-UM algorithm uses a sliding window W(i,j) of size (2b+1)×(2h+1) to scan the input image [X] of size M×N, with pixels x(i,j) (i=1, 2, . . . , M, j=1, 2, . . . , N). FIG. 15 is a block diagram illustrating the FRA-UM algorithm, according to an embodiment of the present subject matter. It corresponds to the FRA-UM algorithm steps given as follows.

Non-recursive adaptive unsharp masking algorithm is calculated in bl. 54:

$$f(i,j) = \begin{cases} f'(i,j) & \text{for } |x(i,j) - \mu_x(i,j)| \geq \delta, \\ x(i,j) & \text{in other cases,} \end{cases} \quad (16)$$

where:

$$f'(i,j) = x(i,j) + \lambda[x(i,j) - \mu_x(i,j)] = \\ x(i,j) + \lambda\left[x(i,j) - (1/N_W)\sum_{k=-b}^{b}\sum_{l=-h}^{h} x(i+k,j+l)\right]. \quad (17)$$

The value of f'(i,j) is calculated in block 53, and that of $$\mu_x(i, j) = (1/N_W) \sum_{k=-b}^{b} \sum_{l=-h}^{h} x(i+k, j+l)$$

in block 52; $N_W=(2b+1)(2h+1)$—the number of pixels in the sliding window W(i,j) of size $(2b+1)\times(2h+1)$; (it is recommended to use a square window W(i,j) of size $(2c+1)\times(2c+1)$ for b=h=c); f(i,j)—a pixel from the sharpened image (in block 55); $\lambda$—a coefficient used to control the sharpness enhancement, whose value is chosen experimentally in the range $0.2<\lambda<0.9$; $\delta$—threshold, $\delta \geq s\sigma_x$ for $0.2<s<0.9$ and $\sigma_x^2$—noise variance in the input image x(i,j). To reduce the calculations, expression (16) is transformed as follows:

$$f'(i, j) = \qquad(18)$$

$$(\lambda/N_W)\left[(N_W/\lambda + N_W - 1)x(i, j) - \sum_{k=-a}^{a}\sum_{l=-b}^{b} x(i+k, j+l)\right] \text{ for }$$

$$(k+l) \neq 0.$$

Figures 16, 17:
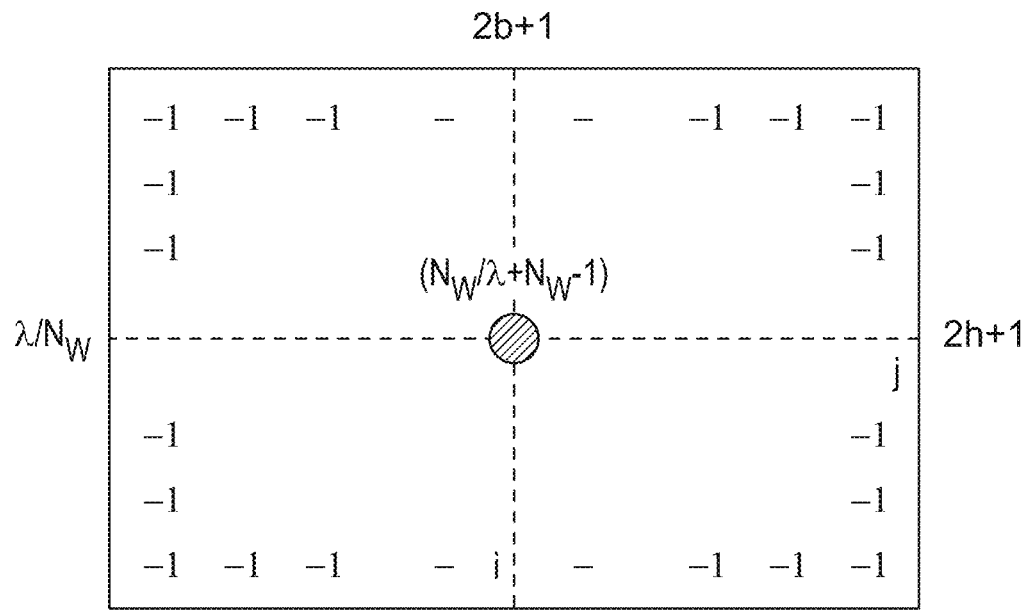
FIG. 16 is an illustration of a kernel of an unsharp masking 2D digital filter, according to an embodiment of the present subject matter.
FIG. 17 is an illustration of an example kernel of unsharp masking 2D digital filter, according to an embodiment of the present subject matter.

Then, in accordance with the above expression, the pixel f'(i,j) is the result of applying the convolution operation of the image with a kernel of two-dimensional (2D) digital filter, given in FIG. 16, which is an illustration for the kernel of the unsharp masking 2D digital filter of size, according to an embodiment of the present subject matter. Through suitable choice of $\lambda$ with respect to the $N_W$ filtration is performed with a 2D kernel, which is an integer matrix. As a result, rounding errors of f'(i,j) are reduced and calculations are accelerated.

Example: 2D digital filter for unsharp masking with the kernel of size 7×7 (a=b=3, $N_W=49$) and $\lambda=0.49$ from relation (16) and FIG. 17, which is an illustration of the kernel of the unsharp masking 2D digital filter of size 7×7, according to an embodiment of the present subject matter. For the acceleration of the calculation of the mean value $\mu_x$, in bl. 52 is used the 2D recursive relation (2).

From the above expression is the following recursive form of calculation in bl. 53:

$$f(i,j)=(1+\lambda)x(i,j)-\lambda[\mu_x(i-1,j)+\mu_x(i,j-1)-\mu_x(i-1,j-1)]-(\lambda/N_W)[x(i+b,j+h)-x(i+b,j-h-1)-x(i-b-1,j+h)+x(i-b-1,j-h-1)].\qquad(19)$$

The number of operations in the last equation is always 12 and does not depend on the filter window size. For the non-recursive case, the value f'(i,j) is calculated by $(2b+1)\times(2h+1)+4$ operations. In case that b>>1 and h>>1, the reduced number $\rho_{2D}$ of arithmetic operations becomes:

$$\rho_{2D}=(1/12)[(2b+1)(2h+1)+4]\approx 0.33\times bh.\qquad(20)$$

For example, if b=h=20 then $\rho_{2D}\approx 133$, i.e., the number of summations necessary for the recursive filter is more than 133 times smaller. This is the advantage of the new approach, presented here.

For further simplification it is possible instead of applying one 2D mean filter, to apply two 1D mean filters—the first over the lines in the horizontal direction of the input image [X], and the second—over the columns in the vertical direction, in accordance with the expressions:

$$\mu_1(i, j) = x(i, j) + \lambda_1\left[x(i, j) - \frac{1}{(2b)+1}\sum_{k=-b}^{b} x(i+k, j)\right];\qquad(21)$$

$$\mu(i, j) = \mu_1(i, j) + \lambda_2\left[\mu_1(i, j) - \frac{1}{(2l+1)}\sum_{l=-h}^{h}\mu_1(i, j+l)\right].$$

Here $\lambda=\lambda_1\times\lambda_2$ and $\mu_1(i,j)$ is the pixel (i,j) of the image obtained in result of the first filtration (in horizontal direction). The above two equations are presented in recursive form of calculation:

$$\mu_1(i, j) = \mu_1(i-1, j) - \frac{\lambda_1}{(2b+1)}[x(i-b-1, j) - x(i+b, j)];\qquad(22)$$

$$\mu(i, j) = \mu(i, j-1) - \frac{\lambda_2}{(2h+1)}[\mu_1(i, j-h-1) - \mu_1(i, j+h)].$$

If $\lambda_1=\lambda_2=\lambda_0=\sqrt{\lambda}$, then the equation for the 2D recursive calculation of $\mu(i,j)$ is replaced by the following equations for 1D recursive calculation of $\mu(i,j)$ in bl. 52:

$$\mu_1(i, j) = \mu_1(i-1, j) - \frac{\lambda_0}{(2b+1)}[x(i-b-1, j) - x(i+b, j)];\qquad(23)$$

$$\mu(i, j) = \mu(i, j-1) - \frac{\lambda_0}{(2h+1)}[\mu_1(i, j-h-1) - \mu_1(i, j+h)].$$

FIG. 18 is an illustration for spatial arrangement of pixels in a sliding line of size $(2b+1)\times(1)$ used for the recursive calculation of the value $\mu_1(i,j)$ in horizontal direction, according to an embodiment of the present subject matter. FIG. 19 is an illustration for spatial arrangement of pixels in a sliding column of size $(1)\times(2h+1)$ used for the recursive calculation of the value $\mu(i,j)$ in vertical direction, according to an embodiment of the present subject matter. FIGS. 18 and 19 show the spatial positions of the pixels by which a 1D recursive calculation of the intermediate image $\mu_1(i,j)$ and the final image $\mu(i,j)$ is performed according to the above expression. The reduced number of arithmetic operations is:

$$\rho_{1D}=(1/4)[(2b+4)+(2h+4)]=(1/2)(b+h)+2.\qquad(24)$$

For example, if b=h=20, then $\rho_{1D}=22$, i.e., in result of the recursive approach the number of summations is more than 22 times smaller. The algorithm efficiency is additionally enhanced in result of the double use of the same 1D filter.

A comparison of recursive 2D and 1D calculations of the pixel $\mu(i,j)$ shows that the 1D calculation is less computational complexity (b/3 times for b=h), but requires double scan of the image, which increases the overall time for filtration.

The algorithm for Linear Mixing (LM) of the filtered, contrasted, and sharpened images is performed in block 6 of the scheme of FIG. 1. The final image with pixels z(i,j) is a linear combination of the image with pixels g(i,j) with enhanced contrast and filtered noise, and the image with pixels f(i,j), whose sharpness was enhanced. In this case, the output image is calculated as follows:

$$z(i,j)=\alpha g(i,j)+(1-\alpha)f(i,j)\qquad(25)$$

for i=b+2, b+3, . . . , M−b and j=h+2, h+3, . . . , N−h, where $\alpha$ is the control coefficient used for the mixing of pixels g(i,j) and f(i,j), whose value is chosen in the range $0<\alpha<1$.

Figure 20A:
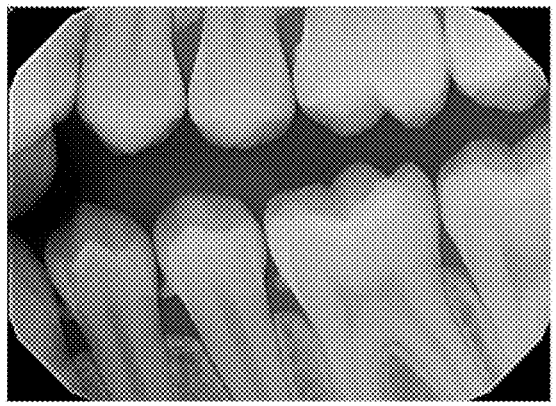
FIGS. 20A-20D are illustrations of an example for X-ray dental image enhancement by the FRA-UM, according to an embodiment of the present subject matter.
Figure 20B:
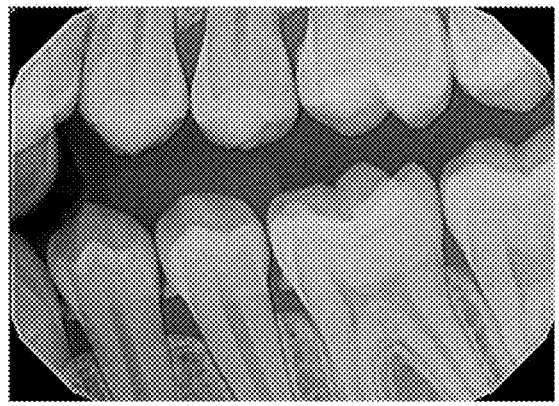
Figure 20C:
Figure 20D:

FIGS. 20A-20D are images showing examples of X-ray dental image enhancement by the FRA-UM, including input X-ray dental image 1 (FIG. 20A), enhanced X-ray dental image 1 (FIG. 20B), input X-ray dental image 2 (FIG. 20C), and enhanced X-ray dental image 1 (FIG. 20D). The main parameters which define the output image, are: q, c, d, λ, α. Their values are defined in the process of testing the image database containing X-rays bitewing images. In the general case the values of these parameters are selected depending on the type and resolution of X-ray dental images and the specific requirements, related with reliable detection of various defects of the imaged teeth. The control of the values of the main parameters is performed in block 7 on the basis of the criteria described below for evaluation of the quality of the obtained image.

For the quantitative evaluation of the image quality enhancement are developed various criteria [22, 23] which correspond to different image classes, as photos, video sequences (grayscale and color), underwater, multispectral, and medical (ultrasound, computer tomography sequences, X-ray photos, etc.). For the evaluation of X-ray dental images were specially chosen the following quantitative metrics:

1. Metrics for Contrast Enhancement Evaluation: Mean Square Difference Entropy (MSDE):

$$MSDE = \text{Mean}(\Delta E^2) = (1/MN)\sum_{i=1}^{M}\sum_{j=1}^{N}\left(LE_{x_{1(i,j)}} - LE_{x_{0(i,j)}}\right)^2, \quad (26)$$

where $$LE_{i,j} = -\sum_{k=0}^{m-1} h_{i,j}(k) \times \log_2[h_{i,j}(k)]$$

Local Entropy (LE) in sliding window; $x_1(i,j)$ and $x_0(i,j)$ are the grey level values of pixels of the output (filtered) and the input (original) image, respectively.

2. Metrics for Image Sharpness Evaluation: Sharpness Index (SI), Based on the Gradient Vector G(i,j)=Grad x(i,j):

$$SI = TGD_{sharpened\ image\ f}/TGD_{original\ image\ x}, \quad (27)$$

$$\text{where } TGD = (1/MN)\sum_{i=1}^{N}\sum_{j=1}^{M}\left\{[G_1(i,j)]^2 + [G_2(i,j)]^2\right\} \quad (28)$$

is Tenengrad gradient function which uses the Sobel operator to extract the horizontal and vertical gradient values:

$$G_1(i,j)=[x(i-1,j-1)+2x(i-1,j)+x(i-1,j+1)]-[x(i+1,j-1)+2x(i+1,j)+x(i+1,j+1)], \quad (29)$$

$$G_2(i,j)=[x(i-1,j+1)+2x(i,j+1)+x(i+1,j+1)]-[x(i-1,j-1)+2x(i,j-1)+x(i+1,j-1)]. \quad (30)$$

Metrics for Noise Reduction Evaluation:
1. Mean Squared Error MSE:

$$\bar{\varepsilon}^2 = (1/MN)\sum_{i=1}^{M}\sum_{j=1}^{N}[x_1(i,j) - x_0(i,j)]^2 \quad (31)$$

2. Signal to Noise Ratio (SNR):

$$SNR = 10\log_{10}\left[\sum_{i=1}^{M}\sum_{j=1}^{N}[x_1(i,j)]^2 \Big/ \sum_{i=1}^{M}\sum_{j=1}^{N}[x_1(i,j) - x_0(i,j)]^2\right][dB] \quad (32)$$

3. Peak Signal to Noise Ratio (PSNR):

$$PSNR = 10\log_{10}[(m-1)^2/\bar{\varepsilon}^2]\ [dB], \quad (33)$$

where m is the number of gray level values, for example m=256 (8 bpp).

On the basis of the above-described criteria, corresponding algorithms for image quality assessment have been used for parameters control in block 7. The control is based on comparing the calculated parameters with preset values. The obtained deviations are used for iterative change of the parameters until they reach values close to the preset ones.

The comparison of the results obtained through applying the algorithm on X-ray dental images enhancement was done by using the Internet-accessible program codes. These results were obtained by non-iterative RSW-CLAHE and FRA-UM for the following values of the basic parameters: q=0.2, c=2, λ=0.4, α=0.4.

Figure 21A:
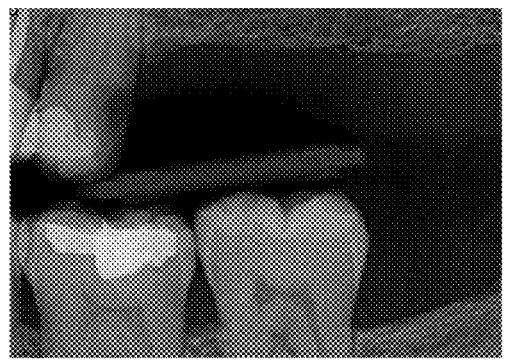
FIGS. 21A-21C are illustrations of an example of an input X-ray dental image (FIG. 21A), an enhanced X-ray dental image by Contrast Limited Histogram Equalization (CLAHE) (FIG. 21B), and a non-iterative RSW-CLAHE+ FRA-UM (FIG. 21C), according to an embodiment of the present subject matter.
Figure 21B:
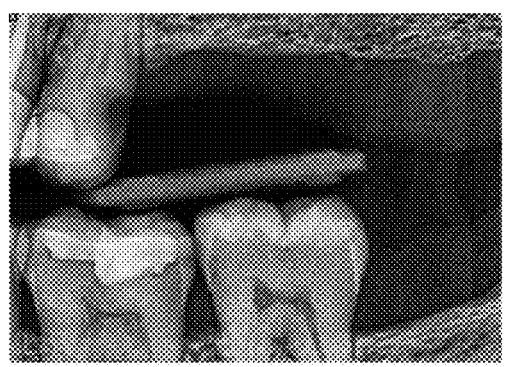
Figure 21C:
Figure 22A:
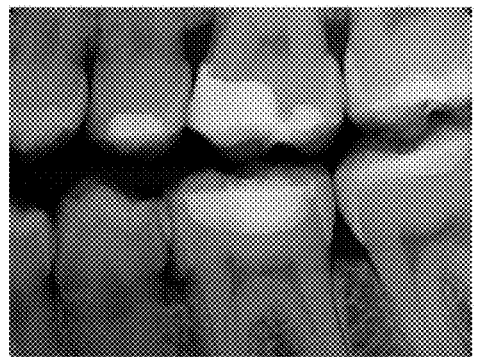
FIGS. 22A-22C are illustrations of another example of an input X-ray dental image (FIG. 22A), an enhanced X-ray dental image by CLAHE (FIG. 22B), and the non-iterative RSW-CLAHE+FRA-UM (FIG. 22C), according to an embodiment of the present subject matter.
Figure 22B:
Figure 22C:
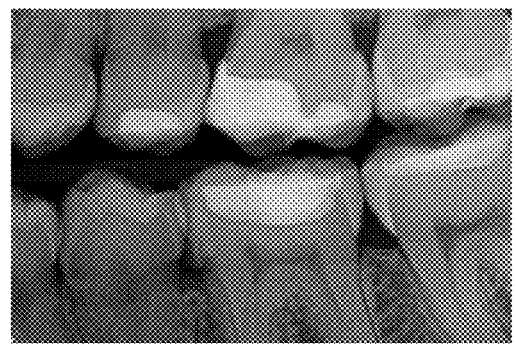

For visual evaluation and quality comparison of the improved X-ray bitewings images through applying the non-iterative RSW-CLAHE+FRA-UM and the CLAHE. FIGS. 21A-21C are images showing an example of an input X-ray dental image (FIG. 21A), an enhanced X-ray dental image by CLAHE (FIG. 21B), and an enhanced X-ray dental image by non-iterative RSW-CLAHE+FRA-UM (FIG. 21C) (sample 1). FIGS. 22A-22C are images showing another example of an input X-ray dental image (FIG. 22A), an enhanced X-ray dental image by CLAHE (FIG. 22B), and non-iterative RSW-CLAHE+FRA-UM (FIG. 22B)(sample 2).

Figure 23A:
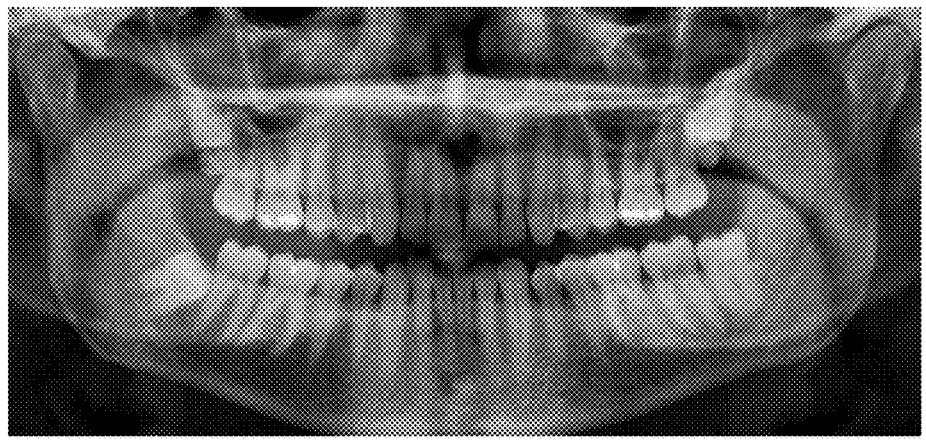
FIGS. 23A-23E are illustrations of an example of enhancement of a X-ray dental panoramic image.
Figure 23B:
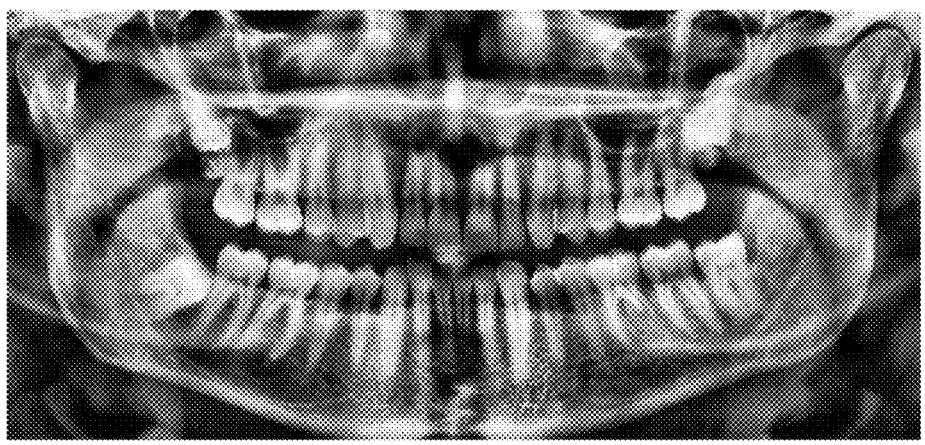
Figure 23C:
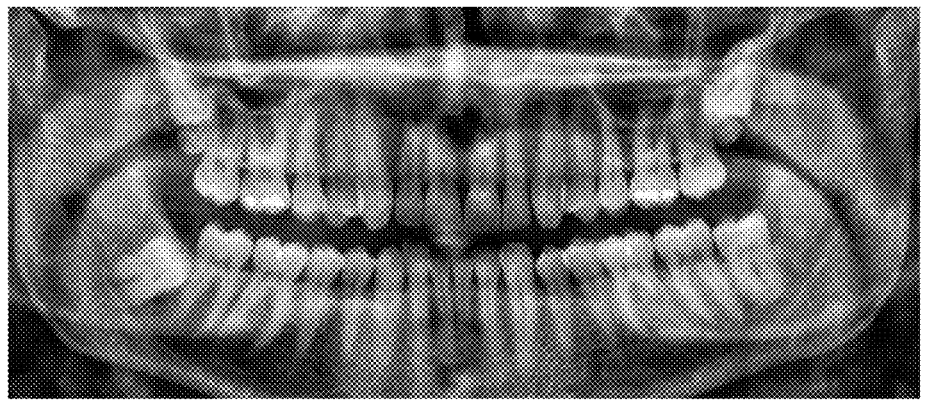
Figure 23D:
Figure 23E:
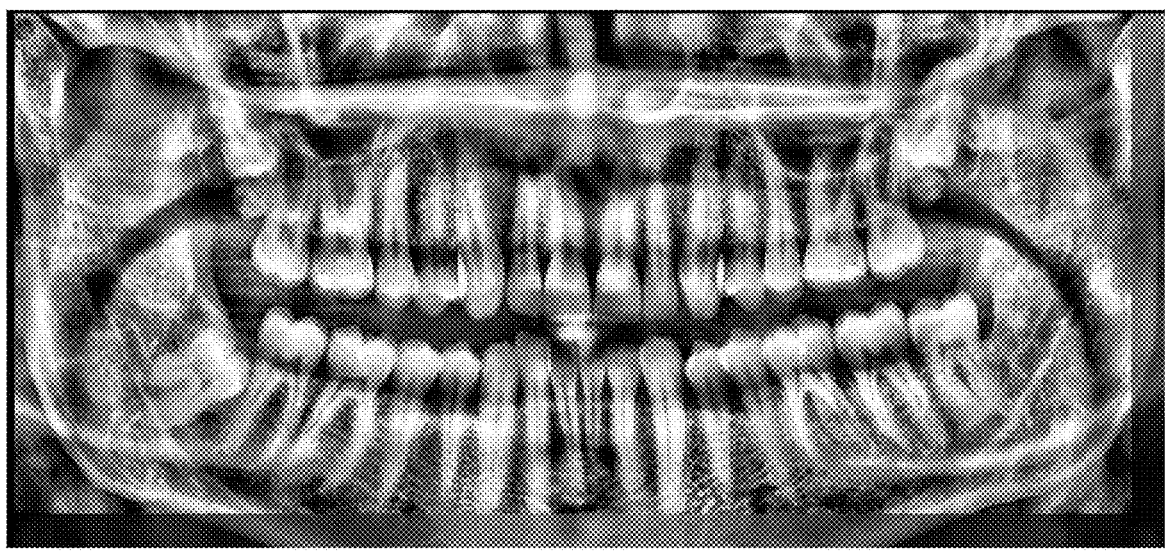

FIGS. 23A-23E are images showing an example of enhancement of a dental X-ray panoramic image. FIG. 23A shows an input dental X-ray panoramic image. FIG. 23B shows enhanced output image by CLAHE, MSDE=4.20 bits. FIG. 23C shows enhanced image by non-iterative RSW-CLAHE for q=0.02 and c=16, MSDE=138.77 bits. FIG. 23D shows enhanced image by non-iterative RSW-CLAHE for q=0.0006 and c=16, MSDE=85.67 bits. FIG. 23E shows enhanced output image by iterative RSW-CLAHE for c=16 and MSDE=30.78 bits.

The visual evaluation of the images from FIGS. 23B, 23C, and 23D shows the advantages of RSW-CLAHE compared to CLAHE for the cases, when must be enhanced the contained information (the improved image c), or the local contract (the improved images d and e). The images from FIGS. 23A-23E could be quantitative evaluated trough the criterion MSDE (25). From the data shown on FIGS. 23B, 23C, 23D, and 23E is seen that for RSW-CLAHE, the corresponding values of MSDE are much higher than these for CLAHE. Besides, from the results shown on FIGS. 23C and 23D is seen that the values of the parameters q and c define the enhancement of the local contrast of the image. The choice of the values of these parameters correspond to the requirements of visual diagnostic.

Figure 24A:
FIGS. 24A-24E are illustrations of an example of enhancement of a X-ray dental periapical image.
Figure 24B:
Figure 24C:
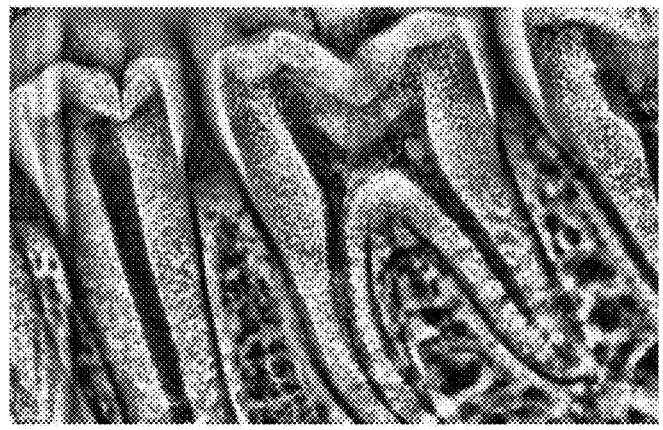
Figure 24D:
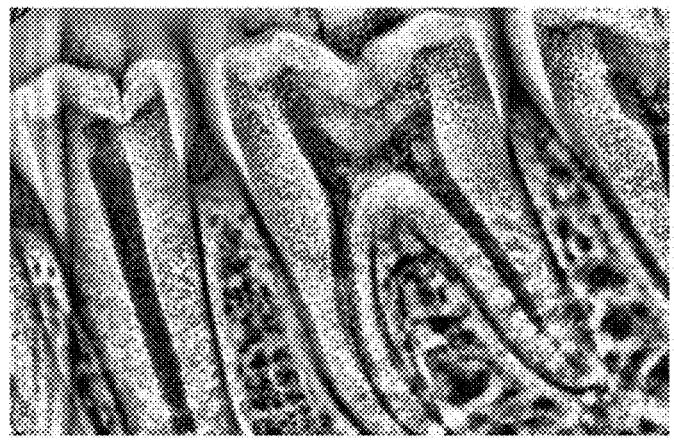
Figure 24E:
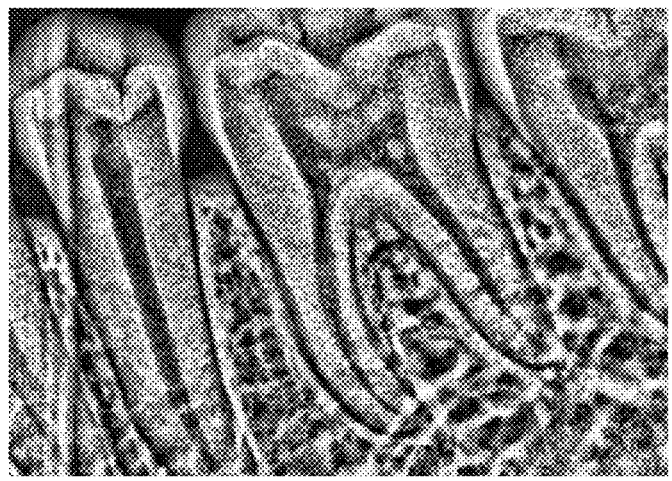

FIGS. 24A-24E are images showing an example of enhancement of a dental X-ray periapical image. FIG. 24A shows an input dental X-ray periapical image. FIG. 24B shows enhanced output image by CLAHE, MSDE=1.57 bits. FIG. 24C shows enhanced image by non-iterative RSW-CLAHE for q=0.02, c=27, MSDE=82.69 bits. FIG. 24D shows enhanced image by non-iterative RSW-CLAHE for q=0.00001, c=16, MSDE=123.27 bits. FIG. 24E shows enhanced output image by iterative RSW-CLAHE for c=16 and MSDE=28.86 bits.

The results of the comparison of the proposed new algorithm for improvement of X-ray bitewings dental images with algorithms CLAHE and Global Histogram Equalization (GHE), are shown in Table 2.

TABLE 2

Metrics for image quality evaluation when using the RSW-CLAHE, compared to CLAHE and GHE

| Evaluation metrics | RSW-CLAHE | CLAHE | GHE |
|---|---|---|---|
| mean MSDE, bits | 1.12 | 0.42 | 0.15 |
| mean SI, bits | 1.72 | 1.01 | 0.97 |
| mean SNR, [dB] | 29.54 | 17.17 | 13.97 |
| mean PSNR, [dB] | 34.70 | 21.90 | 18.67 |

The objective quality of the improved images is evaluated by using the metrics based on the criteria MSDE, SI and PSNR. A mean evaluation was done of the quality of 1868 test X-rays bitewing images, improved by applying the proposed RSW-CLAHE algorithm, CLAHE and GHE, based on the mean value of MSDE, SI, SNR and PSNR.

Figure 25:
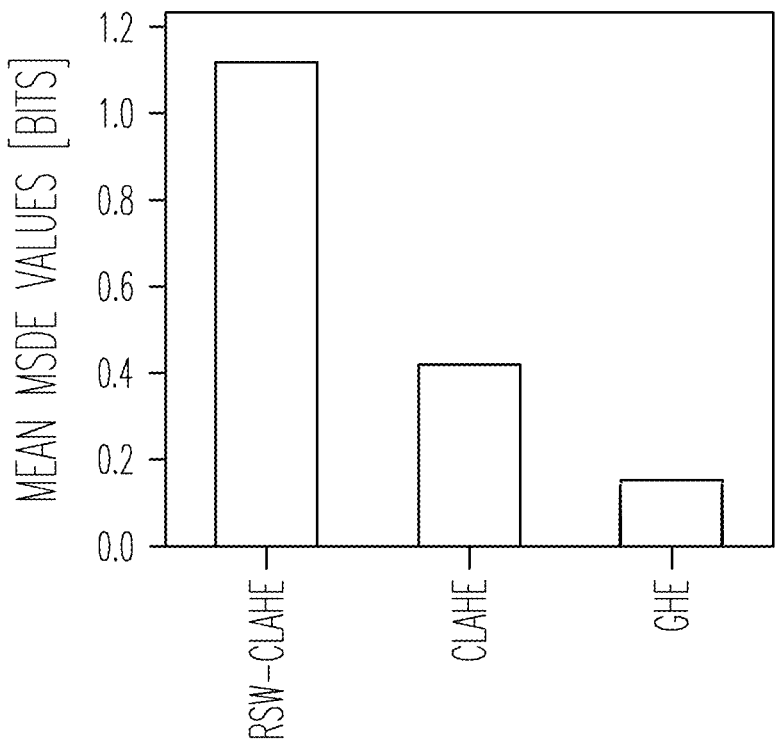
FIG. 25 is an illustration of a mean value of MSDE for contrast evaluation through the non-iterative RSW-CLAHE according to an embodiment of the present subject matter, CLAHE, and Global Histogram Equalization (GHE).
Figure 26:
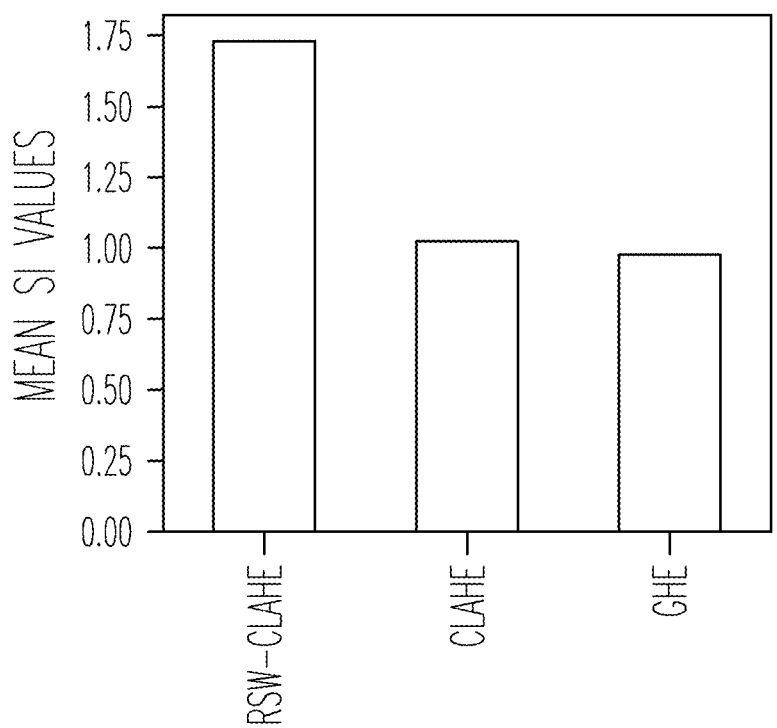
FIG. 26 is an illustration of a mean value of SI for sharpness evaluation through the non-iterative RSW-CLAHE according to an embodiment of the present subject matter, CLAHE, and GHE.
Figure 27:
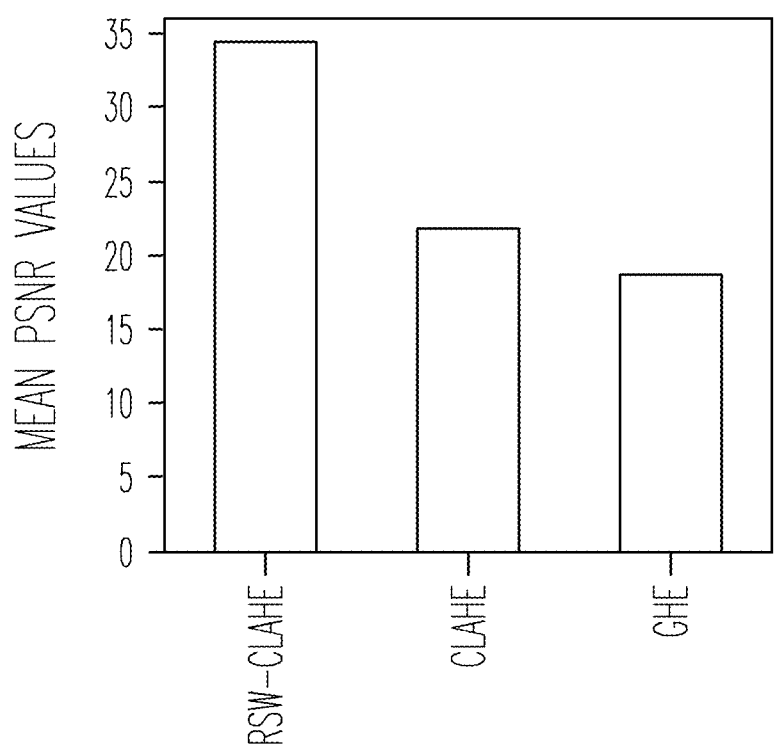
FIG. 27 is an illustration of a mean value of PSNR for noise evaluation through the non-iterative RSW-CLAHE according to an embodiment of the present subject matter, CLAHE, and GHE.

The obtained results are shown in FIGS. 25, 26, and 27. FIG. 25 is graph of mean value of MSDE for contrast evaluation through RSW-CLAHE, CLAHE, and GHE. FIG. 26 is graph of mean value of SI for sharpness evaluation through RSW-CLAHE, CLAHE, and GHE. FIG. 27 is graph of mean value of PSNR for noise evaluation through RSW-CLAHE, CLAHE, and GHE. The obtained quantitative results confirm the advantages of the proposed RSW-CLAHE compared to CLAHE and GHE in respect of criteria MSDE, SI and SNR, used for the evaluation of X-ray dental images.

Figure 28:
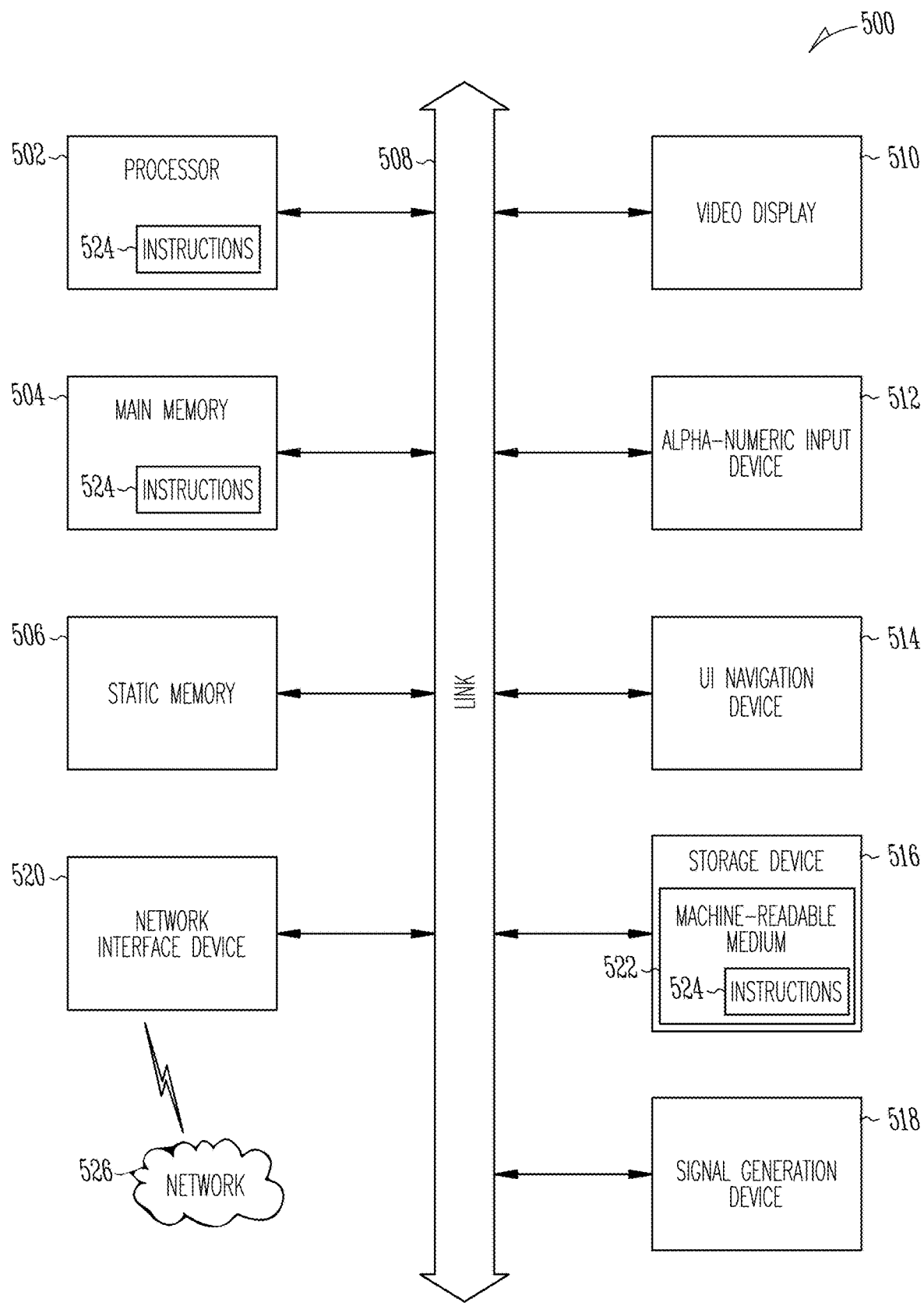
FIG. 28 is a block diagram illustrating a machine in a form of a computer system, according to an embodiment of the present subject matter.

FIG. 28 is a block diagram illustrating a machine in an example form of a computer system 500, according to an embodiment of the present subject matter. Within the computer system 500, a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments.

The machine may be a Personal Computer (PC), a tablet PC, a hybrid tablet, a Set-Top Box (STB), a Personal Digital Assistant (PDA), a mobile or cellular telephone such as a smart phone, a wearable device such as a smart watch, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 500 may include one or more of the following: processor 502 (e.g., a Central Processing Unit (CPU), a Graphics Processing Unit (GPU) or both, processor cores, compute nodes, etc.), a main memory 504 and a static memory 506, which communicate with each other via a link 508 (e.g., bus). The computer system 500 may further include a video display unit 510, an alphanumeric input device 512 (e.g., a keyboard), and a User Interface (UI) navigation device 514 (e.g., a mouse). In one embodiment, the video display unit 510, input device 512 and UI navigation device 514 are incorporated into a touch screen display. The computer system 500 may additionally include a storage device 516 (e.g., a drive unit), a signal generation device 518 (e.g., a speaker), a network interface device 520, and one or more sensors (not shown), such as a Global Positioning System (GPS) sensor, compass, accelerometer, or other sensor.

The data storage device 516 includes a machine-readable medium 522 on which is stored one or more sets of data structures and instructions 524 (e.g., software) embodying or utilized by any one or more of the methodologies or functions described herein. The instructions 524 may include a machine learning system or algorithm, and may also reside, completely or at least partially, within the main memory 504, static memory 506, and/or within the processor 502 during execution thereof by the computer system 500, with the main memory 504, static memory 506, and the processor 502 also constituting machine-readable media.

While the non-transitory computer-readable storage medium 522 is illustrated in an example embodiment to be a single medium, the term "machine-readable medium" or "computer-readable medium" may include a single medium or multiple media (e.g., a centralized or distributed database, and/or associated caches and servers) that store the one or more instructions 524.

The term "machine-readable medium" shall also be taken to include any tangible medium that is capable of storing, encoding or carrying instructions (e.g., instructions 524) for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media.

Specific examples of machine-readable media include non-volatile memory, including, but not limited to, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of known Hypertext Transfer Protocols (e.g., HTTP).

Examples of communication networks include a Local Area Network (LAN), a Wide Area Network (WAN), the Internet, mobile telephone networks, Plain Old Telephone System (POTS) networks, and wireless data networks (e.g., Wi-Fi, 3G, and 6G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure, for example, to comply with 37 C.F.R. § 1.72(b) in the United States of America. It is submitted with the understanding that it will not be used to interpret or limit the scope or meaning of the claims.

Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

One advantage of the present subject matter is that unlike the known methods, it is fully adaptive to the local statistical qualities of the analyzed X-ray dental images. This quality permits to achieve higher efficiency in the correction of the existing shortcomings of the kind:

Grey level transition blur which could vary in the central and peripheral areas of the image;

Low contrast with irregular distribution in the different parts of the image;

Irregularly distributed noise;

Irregularities in the image background;

One of the characteristics that this method distinguishes from known methods is its recursive scheme for calculation of the enhanced image. In result, the image processing is significantly accelerated.

Some of the differences and advantages of the new method in each of the described stages include:

Recursive Locally-Adaptive Wiener Filtration (RLA-WF) of pixels in the sliding window. To calculate the average value of these pixels, a two-dimensional recursive scheme is applied, which adds an advantage by speeding up the calculation of the filtered central pixel of the window. The second advantage of the RLA-WF compared to the known adaptive Wiener filtering is that it is adaptive towards the level of the local variation compared to the global one, in result of which are retained the transitions in the image, while the noise is suppressed;

Local contrast enhancement based on new algorithm, called Recursive Sliding Window Contrast Limited Adaptive Histogram Equalization (RSW-CLAHE)— iterative and non-iterative. The algorithm is adaptive towards the local statistics of the pixels framed by the sliding window. For this is first calculated the local histogram, its maximum is limited by using TTS and the so modified histogram is equalized, so that the contrast to be enhanced in a limited range of greyscale values. In comparison the known algorithm SWAHE (Sliding Window Adaptive Histogram Equalization) does not use a limitation of the maximum value of the local histogram in the sliding window. The difference between the offered algorithm and the known CLAHE (Contrast Limited Adaptive Histogram Equalization) is in the fact that CLAHE does not use a sliding window where the image quality to be enhanced in accordance with the local statistics of the framed part of the image. Instead, there are calculated the so-called "conceptual regions in the image" for which CLAHE is applied. The new algorithm RSW-CLAHE differs both from SWAHE and CLAHE in the performance: the calculations in RSW-CLAHE are based on new two-dimensional recursive scheme which accelerates the image processing;

Adaptation of RSW-CLAHE towards local statistics of the pixels framed by the sliding window through calculation of an individual threshold CL for clipping the local histogram of the pixels in the window. For this, bilinear interpolation (BLI) at 4 reference values is used to calculate a surface which to define the local threshold CL. The image is divided in advance into non-overlapping blocks and for each, the threshold CL is defined. For each 4 neighbor reference values is performed BLI. Determination of the threshold CL based on the pre-calculated interpolated threshold surface significantly reduces the computational complexity compared to the case where CL is calculated by analyzing the local histogram of the pixels in the sliding window;

Sharpness enhancement based on the Fast Recursive Adaptive Unsharp Masking (FRA-UM) method, which differs from the known methods according to the proposed new approaches for controlling the degree of sharpening depending on the local statistics of the pixels in the sliding window around the central pixel. The first scheme is based on two-dimensional recursion, and the second—on one-dimensional recursion, which is performed by a simple algorithm, but requires double scanning of the image. Another difference of the new approach is that it allows to control the sharpness enhancement based on the local statistics in the sliding window around the central pixel;

Linear Mixing (LM) the obtained two images is proposed: the first is with filtered noise and enhanced contrast, and the second—with enhanced sharpness. The image, obtained in result, could be with predominance of the first, or of the second image, depending on the users' requirements.

The presented sequence of processing stages is unique and is not used in existing methods.

The result obtained in accordance with the new method depends on the choice of several basic parameters. In this way, easy adaptation is possible to the processed image, which could be of various size and bits per pixel (bpp). Another difference and advantage is that this new method does not cause distortions in the edges of the image, which happen in many other prior art methods.

Due to its low computational complexity, the method could be implemented not only in software, but also in hardware or firmware. The stages of the processing related to the filtration and contrast enhancement on the one hand, and the sharpness enhancement on the other hand, could be executed in parallel, depending of the kind of the used computer platform.

The offered method could be used for single images and/or for each image in Computer Tomography Image (CTI) sequence by using the corresponding most suitable settings of the participating parameters.

Some non-limiting examples of the present subject matter are provided as follows:

In Example 1, a method for enhancing an X-ray dental image is provided. The method may include: applying noise filtration to an input X-ray dental image, including using Recursive Locally-Adaptive Wiener Filtration (RLA-WF) based on a sliding window calculated following a 2-dimensional (2D) recursive scheme; applying contrast enhancement to the input X-ray dental image, using Recursive Sliding Window Contrast Limited Adaptive Histogram Equalization (RSW-CLAHE) utilizing a Truncation Threshold Surface (TTS), and the sliding window to obtain an enhanced output image; applying sharpness enhancement to the input X-ray dental image, using Fast Recursive Adaptive Unsharp Masking (FRA-UM) utilizing the sliding window, to obtain a sharpened image by 2D recursive scheme or a 1-dimensional (1D) recursive scheme based on double scanning of the X-ray dental image; and linearly mixing (LM) the noise filtrated and contrast enhanced X-ray dental image with the sharpness enhanced X-ray dental image using a control coefficient in order to obtain an output X-ray dental image.

In Example 2, the subject matter of Example 1 may optionally further include some or all of:
  a) calculating a locally-adaptive Wiener filtration based on sliding window and calculation following a new recursive 2D scheme;
  b) calculating Truncation Threshold Surface (TTS), by which to determine an individual threshold for trimming of the local histogram of the pixels in the sliding window around each current pixel;
  c) dividing the image into blocks whose size increases for high resolution image;
  d) calculating an individual threshold for each block;
  e) evaluating a surface of the individual threshold for each pixel based on bilinear interpolation from each four adjacent blocks, containing this pixel;
  f) calculating a local histogram of pixels of input image using a sliding window;
  g) separating the local histogram into parts using a truncation threshold;
  h) calculating a modified histogram from the parts of the local histogram using an iterative or non-iterative RSW-CLAHE algorithm;
  i) calculating a new recursive cumulative modified local histogram from the modified histogram;
  j) calculating a grey level of a first pixel from an enhanced input image based on the recursive cumulative modified local histogram;
  k) moving a sliding window one position ahead in a horizontal direction to a second pixel;
  l) repeating the above steps (a-k) for the second and subsequent pixels of the image, wherein the truncation threshold is obtained by using the Truncation Threshold Surface;
  m) applying a recursive algorithm for image sharpness enhancement using fast recursive adaptive Unsharp masking by new 2D recursive scheme or by simpler new 1D recursive scheme based on double scanning of the image;
  n) selecting a type of recursion (2D or 1D) depend on the time limits for implementation of calculations;
  o) performing a linear mixing of de-noised and contrast enhanced pixels and sharpened pixels with different weighting coefficients to obtain an pixels of the output image; and
  p) selecting of the values of these coefficients by the user depending on his specific requirements.

This document is intended to cover adaptations or variations of the present subject matter. It is to be understood that the above detailed description is intended to be illustrative, and not restrictive. Other embodiments will be apparent to those of skill in the art upon reading and understanding the above description. The scope of the present subject matter should be determined with reference to the appended claims, along with the full scope of legal equivalents to which such claims are entitled.

REFERENCES

1. A. Goharrizi, M. Rezaee, Method and Apparatus for Enhancing Medical Images, U.S. Patent Application Publication No. US 2014/0153793 A1, Jun. 5, 2014.
2. Z. Huo, Z. Lao, F. Xu, Enhanced Visualization for Medical Images, U.S. Pat. No. 8,861,886 B2, Oct. 14, 2014.
3. M. Roomi, G. Ganesan, A Review of Image Contrast Enhancement Methods and Techniques, Research Journal of Applied Sciences, Engineering and Technology 9(5): 309-326, 2015.
4. K. Kamalanand, B. Thayumanavan, P. Mannar Jawahar, Computational Techniques for Dental Image Analysis, IGI Global Publisher, 2019, pages 334, DOI: 10.4018/978-1-5225-6243-6.
5. R. Hummel, Image Enhancement by Histogram Transformation. Computer Graphics and Image Processing, 6, 1977, 184195.
6. C. Rubini, N. Pavithra, Contrast Enhancement of MRI Images using AHE and CLAHE Techniques, International Journal of Innovative Technology and Exploring Engineering, Vol. 9 Issue 2, December 2019.
7. T. Sund, A. Møystad, Sliding Window Adaptive Histogram Equalization of Intra-oral Radiographs: Effect on Diagnostic Quality. Dentomaxillofac Radiology, May 2006, 35(3), pp. 133-138.
8. K. Zuiderveld, Contrast Limited Adaptive Histogram Equalization. In: P. Heckbert, Graphics Gems IV, Academic Press, 1994.
9. H. Zhu, F. H. Chan, and F. K. Lam, Image Contrast Enhancement by Constrained Local Histogram Equalization, Computer Vision and Image Understanding, 1999, 73(2), pp. 281-290, DOI: 10.1006/cviu.1998.0723.
10. Y. Mohamed Y. Abdallah and T. Alqahtani. Research in Medical Imaging Using Image Processing Techniques, Book chapter in "Medical Imaging. Principles and Applications", Y. Zhou (Ed.), IntechOpen, June 2019, DOI: 10.5772/intechopen.84360.
11. S. Amiri, E. Moudi, Image quality enhancement in digital panoramic radiograph, Journal of AI and Data Mining, Vol. 2, No. 1, 2014, 1-6.
12. G. Campos, S. Mastelini, G. Aguiar, R. Mantovani, L. Melo and S. Barbon. Machine learning hyper-parameter selection for Contrast Limited Adaptive Histogram Equalization, EURASIP Journal on Image and Video Processing, 2019, 2019:59, pp. 1-18, DOI: 10.1186/s13640-019-0445-4.
13. V. Georgieva, R. Kountchev, I. Draganov, An Adaptive Enhancement of X-ray Images, Book chapter in "Advances in Intelligent Analysis of Medical Data and Decision Support Systems", R. Kountchev and B. Iantovics (Eds.), Springer, 2014, pp. 79-88.
14. H. Qassim, N. Basheer, M. Farhan, Brightness Preserving Enhancement for Dental Digital X-ray Images Based on Entropy and Histogram Analysis, Journal of Applied Science and Engineering, Vol. 22, No. 1, pp. 187-194, 2019, DOI: 10.6180/jase.201903_22(1).0019.
15. B. Min, D. Lim, S. Kim, J. Lee, A Novel Method of Determining Parameters of CLAHE based on Image Entropy, International Journal of Software Engineering and Its Applications, Vol. 7, No. 5, 2013, pp. 113-120.
16. K. Kokufuta, T. Maruyama. Real-Time Processing of Contrast Limited Adaptive Histogram Equalization on FPGA. Proceedings of the 2010 International Conference on Field Programmable Logic and Applications, pp. 155-158. IEEE, August 2010, http://ieeexplore.ieee.org/document/5694237/.
17. A. Polesel, G. Ramponi, and V. Mathews. Image Enhancement via Adaptive Unsharp Masking. IEEE Trans. on Image Processing, 9.3. 2000, pp. 505-510.
18. C. Westin, H. Knutsson, R. Kikinis, Adaptive Image Filtering, In "Handbook of Medical Imaging", I. Bankman (Ed.), Academic Press, 2000, pp. 1-22.
19. D. Thanh, V. Prasath, L. Hieu, A Review on CT and X-Ray Images Denoising Methods, Informatica, 43, 2019, pp. 151-159.
20. F. Jin, P. Fieguth, L. Winger and E. Jernigan, Adaptive Wiener Filtering of Noisy Images and Image Sequences, Proceedings of the International Conference on Image Processing, 14-17 Sep. 2003, Barcelona, Spain, DOI: 10.1109/ICIP.2003.1247253.
21. Y. Zhou, C. Shi, B. Lai, G. Jimenez, Contrast enhancement of medical images using a new version of the World Cup Optimization algorithm, Quantitative Imaging in Medicine and Surgery, Vol 9, No 9 Sep. 2019, pp. 1528-1547, doi: 10.21037/qims.2019.08.19.
22. Sharpness Evaluation Method without Reference Image (Evaluation Index for Image Sharpness) https://www.programmersought.com/article/6056166465.
23. V. Jaya, R. Gopikakumari, IEM: A New Image Enhancement Metric for Contrast and Sharpness Measurements, International Journal of Computer Applications, Vol. 79, No. 9, October 2013, pp. 1-9.

What is claimed is:

1. A method, comprising:
applying noise filtration to an input X-ray dental image, including using Recursive Locally-Adaptive Wiener Filtration (RLA-WF) based on a sliding window calculated following a 2-dimensional (2D) recursive scheme to obtain a noise filtrated image;
applying contrast enhancement to the input X-ray dental image, including using Recursive Sliding Window Contrast Limited Adaptive Histogram Equalization (RSW-CLAHE) utilizing a Truncation Threshold Surface (TTS), and the sliding window to obtain a contrast enhanced image;
applying sharpness enhancement to the input X-ray dental image, including using Fast Recursive Adaptive Unsharp Masking (FRA-UM) utilizing the sliding window to obtain a sharpened image by a 2-dimensional (2D) recursive scheme or a 1-dimensional (1D) recursive scheme, the 1D recursive scheme based on double scanning of the X-ray dental image; and
linearly mixing the noise filtrated image and the contrast enhanced image with the sharpened image using a control coefficient to produce an output X-ray dental image.

2. The method of claim 1, wherein applying the sharpness enhancement to the input X-ray dental image comprises using FRA-UM utilizing the sliding window to obtain a sharpened image by the 2D recursive scheme.

3. The method of claim 1, wherein applying the sharpness enhancement to the input X-ray dental image comprises using FRA-UM utilizing the sliding window to obtain a sharpened image by the 1D recursive scheme based on the double scanning of the X-ray dental image.

4. The method of claim 1, wherein applying the contrast enhancement to the input X-ray dental image comprises:
calculating a local histogram of pixels of input X-ray dental image using the sliding window;
separating the local histogram into parts using a truncation threshold;
calculating a modified histogram from the parts of the local histogram using the RSW-CLAHE;
calculating a recursive cumulative modified local histogram from the modified histogram;
calculating a grey level of a current pixel from an enhanced input X-ray dental image based on the recursive cumulative modified local histogram;
moving the sliding window to a next pixel; and
repeating the calculating the local histogram of pixels, separating the local histogram, calculating the modified histogram, calculating the recursive cumulative modified local histogram, calculating a grey level, and moving the sliding window for each pixel of remaining pixels of the input X-ray dental image.

5. The method of claim 4, wherein using the RSW-CLAHE comprises using an iterative RSW-CLAHE algorithm.

6. The method of claim 4, wherein using the RSW-CLAHE comprises using a non-iterative RSW-CLAHE algorithm.

7. The method of claim 4, comprising producing the truncation threshold by calculating the TTS to determine an individual threshold for trimming of the local histogram in the sliding window around the current pixel.

8. The method of claim 7, wherein producing the truncation threshold comprises:
dividing the input X-ray dental image into non-overlapping blocks;
calculating the individual threshold for each block of the blocks; and
evaluating a surface of the individual threshold for the each block based on bilinear interpolation from four blocks of the blocks adjacent the each block.

9. The method of claim 1, selecting the 2D recursive scheme or the 1D recursive scheme based on time limits for implementing calculations.

10. The method of claim 1, comprising using the FRA-UM utilizing the sliding window to obtain a sharpened image by the 2D recursive scheme.

11. The method of claim 1, comprising using the FRA-UM utilizing the sliding window to obtain a sharpened image by the 1D recursive scheme.

12. The method of claim 1, wherein linearly mixing the noise filtrated image and the contrast enhanced image with the sharpened image comprises using weighting coefficients each applied to the noise filtrated image, the contrast enhanced image, and the sharpened image.

13. The method if claim 12, further comprising selecting values of the weighting coefficients based on requirements for the output X-ray dental image.

14. The method if claim 13, further comprising receiving values of the weighting coefficients from a user.

15. An apparatus for enhancing X-ray dental images, the apparatus comprising a processor configured to:
receive an input X-ray dental image;
apply noise filtration to the input X-ray dental image, including using Recursive Locally-Adaptive Wiener Filtration (RLA-WF) based on a sliding window calculated following a 2-dimensional (2D) recursive scheme to obtain a noise filtrated image;

apply contrast enhancement to the input X-ray dental image, including using Recursive Sliding Window Contrast Limited Adaptive Histogram Equalization (RSW-CLAHE) utilizing a Truncation Threshold Surface (TTS), and the sliding window to obtain a contrast enhanced image;

apply sharpness enhancement to the input X-ray dental image, including using Fast Recursive Adaptive Unsharp Masking (FRA-UM) utilizing the sliding window to obtain a sharpened image by a 2-dimensional (2D) recursive scheme or a 1-dimensional (1D) recursive scheme, the 1D recursive scheme based on double scanning of the X-ray dental image; and produce an output X-ray dental image by linearly mixing the noise filtrated image and the contrast enhanced image with the sharpened image.

16. The apparatus of claim 15, wherein the processor is configured to:
calculate a local histogram of pixels of input X-ray dental image using the sliding window;
separate the local histogram into parts using a truncation threshold;
calculate a modified histogram from the parts of the local histogram using an iterative or non-iterative RSW-CLAHE algorithm;
calculate a recursive cumulative modified local histogram from the modified histogram;
calculate a grey level of a current pixel from an enhanced input X-ray dental image based on the recursive cumulative modified local histogram;
move the sliding window to a next pixel; and
repeat the calculating the local histogram of pixels, separating the local histogram, calculating the modified histogram, calculating the recursive cumulative modified local histogram, calculating a grey level, and moving the sliding window for each pixel of remaining pixels of the input X-ray dental image.

17. The apparatus of claim 16, wherein the processor is configured to:
divide the input X-ray dental image into non-overlapping blocks;
calculate the individual threshold for each block of the blocks;
evaluate a surface of the individual threshold for the each block based on bilinear interpolation from four blocks of the blocks adjacent the each block; and
produce the truncation threshold using an outcome of the evaluation of the surface of the individual threshold for the each block.

18. The apparatus of claim 15, wherein the processor is configured to:
receive weighting coefficients for the noise filtrated image, the contrast enhanced image, and the sharpened image;
apply the received respective weighting coefficients to the noise filtrated image, the contrast enhanced image, and the sharpened image; and
linearly mix the weighted noise filtrated image and the weighted contrast enhanced image with the weighted sharpened image.

19. A non-transitory computer-readable storage medium including instructions, which when executed by a machine, cause the machine to perform a method comprising:

applying noise filtration to an input X-ray dental image, including using Recursive Locally-Adaptive Wiener Filtration (RLA-WF) based on a sliding window calculated following a 2-dimensional (2D) recursive scheme to obtain a noise filtrated image;

applying contrast enhancement to the input X-ray dental image, including using Recursive Sliding Window Contrast Limited Adaptive Histogram Equalization (RSW-CLAHE) utilizing a Truncation Threshold Surface (TTS), and the sliding window to obtain a contrast enhanced image;

applying sharpness enhancement to the input X-ray dental image, including using Fast Recursive Adaptive Unsharp Masking (FRA-UM) utilizing the sliding window to obtain a sharpened image by a 2-dimensional (2D) recursive scheme or a 1-dimensional (1D) recursive scheme, the 1D recursive scheme based on double scanning of the X-ray dental image; and linearly mixing the noise filtrated image and the contrast enhanced image with the sharpened image using a control coefficient to produce an output X-ray dental image.

20. The non-transitory computer-readable storage medium of claim 19, wherein applying the contrast enhancement to the input X-ray dental image comprises:
calculating a local histogram of pixels of input X-ray dental image using the sliding window;
separating the local histogram into parts using a truncation threshold;
calculating a modified histogram from the parts of the local histogram using an iterative or non-iterative RSW-CLAHE algorithm;
calculating a recursive cumulative modified local histogram from the modified histogram;
calculating a grey level of a current pixel from an enhanced input X-ray dental image based on the recursive cumulative modified local histogram;
moving the sliding window to a next pixel; and
repeating the calculating the local histogram of pixels, separating the local histogram, calculating the modified histogram, calculating the recursive cumulative modified local histogram, calculating a grey level, and moving the sliding window for each pixel of remaining pixels of the input X-ray dental image.

21. The non-transitory computer-readable storage medium of claim 20, comprising producing the truncation threshold, including:
dividing the input X-ray dental image into non-overlapping blocks;
calculating the individual threshold for each block of the blocks;
evaluating a surface of the individual threshold for the each block based on bilinear interpolation from four blocks of the blocks adjacent the each block; and
producing the truncation threshold using an outcome of the evaluation of the surface of the individual threshold for the each block.

22. The non-transitory computer-readable storage medium of claim 19, wherein linearly mixing the noise filtrated image and the contrast enhanced image with the sharpened image comprises using weighting coefficients each applied to the noise filtrated image, the contrast enhanced image, and the sharpened image.

* * * * *